(12) United States Patent
Morikis et al.

(10) Patent No.: US 10,259,824 B2
(45) Date of Patent: Apr. 16, 2019

(54) COMPLEMENT C3D-BINDING COMPOUNDS

(71) Applicant: The Regents of the University of California, Oakland, CA (US)

(72) Inventors: Dimitrios Morikis, Riverside, CA (US); Ronald D. Gorham, Jr., Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/567,953

(22) PCT Filed: May 1, 2016

(86) PCT No.: PCT/US2016/030335
§ 371 (c)(1),
(2) Date: Oct. 19, 2017

(87) PCT Pub. No.: WO2016/179057
PCT Pub. Date: Nov. 10, 2016

(65) Prior Publication Data
US 2018/0141958 A1    May 24, 2018

Related U.S. Application Data

(60) Provisional application No. 62/156,176, filed on May 1, 2015.

(51) Int. Cl.
| | | |
|---|---|---|
| *C07D 495/04* | (2006.01) |
| *C07D 249/04* | (2006.01) |
| *C07D 417/14* | (2006.01) |
| *C07D 471/04* | (2006.01) |
| *A61P 27/02* | (2006.01) |
| *A61K 31/165* | (2006.01) |

(52) U.S. Cl.
CPC .......... *C07D 495/04* (2013.01); *A61K 31/165* (2013.01); *A61P 27/02* (2018.01); *C07D 249/04* (2013.01); *C07D 417/14* (2013.01); *C07D 471/04* (2013.01)

(58) Field of Classification Search
CPC .. C07D 495/04; C07D 249/09; C07D 417/14; C07D 471/04; A61P 27/02; A61K 31/165
See application file for complete search history.

(56) References Cited

U.S. PATENT DOCUMENTS

2013/0078245 A1* 3/2013 Holers .................. C07K 16/18
424/134.1

OTHER PUBLICATIONS

Wittmann-Regis, Agnes, International Preliminary Report on Patentability and Written Opinion, The International Bureau of WIPO, PCT/US2016/030335, dated Nov. 16, 2017.
Amaro, Rommie E. et al., "An improved relaxed complex scheme for receptor flexibility in computer-aided drug design", J. Comput. Aided Mol. Des., 2008, 22:693-705.
PubChem CID 25598493, Create Date May 27, 2009, pp. 1-11.
Young, Lee W., International Search Report and Written Opinion, U.S. Patent and Trademark Office, PCT/US2016/030335, Aug. 5, 2016.

* cited by examiner

*Primary Examiner* — Timothy R Rozof
(74) *Attorney, Agent, or Firm* — Gavrilovich, Dodd & Lindsey LLP

(57) ABSTRACT

The disclosure provides for compounds that bind with a high affinity to the C3d component of complement. The disclosure further provides for the use of the C3d-binding compounds as therapeutic and/or diagnostic agents for complement-mediated diseases or disorders.

16 Claims, 21 Drawing Sheets

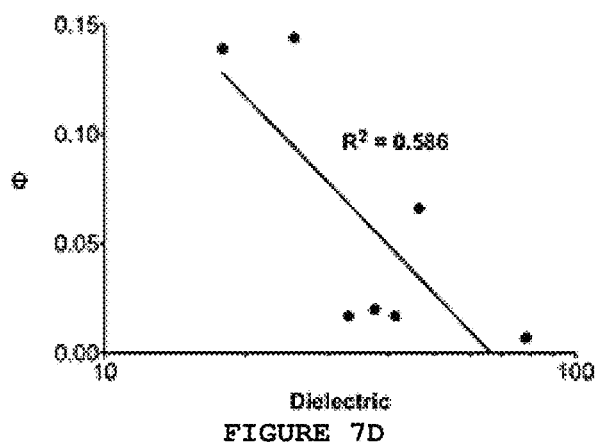
FIGURE 7D
a
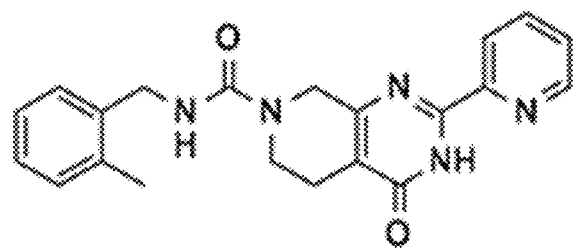
b
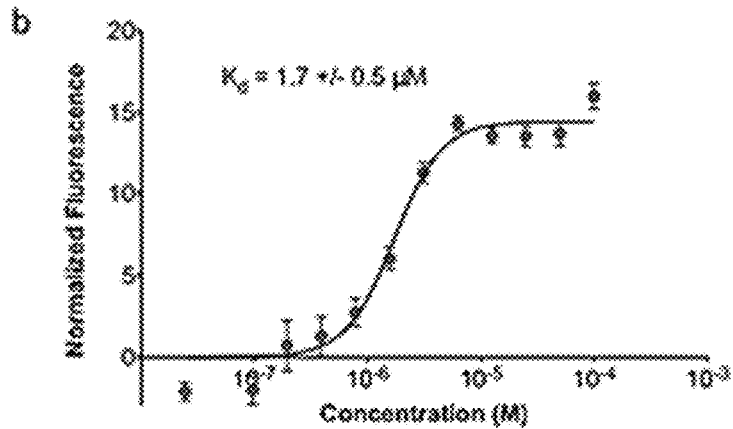
FIGURE 8A-B

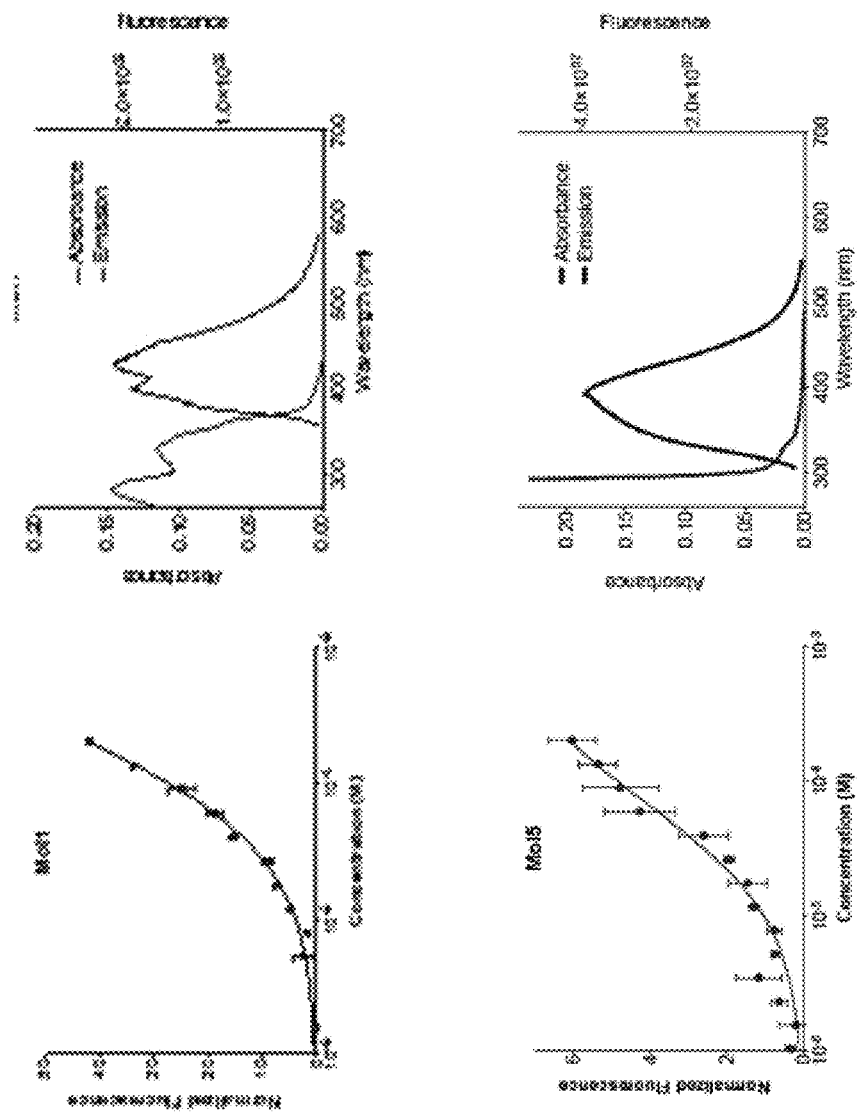
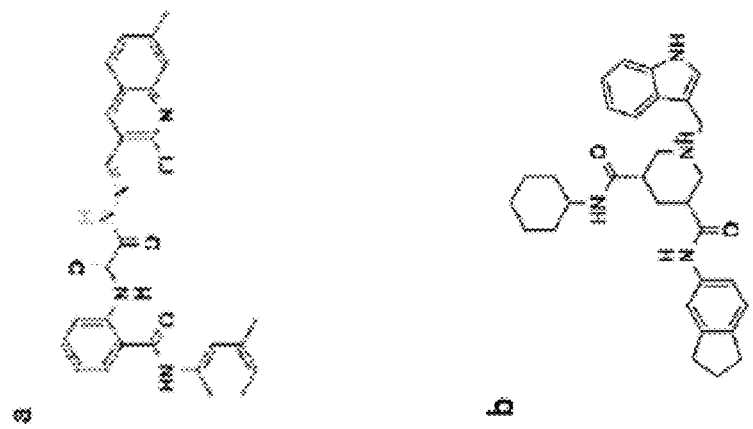
FIGURE 9A-B

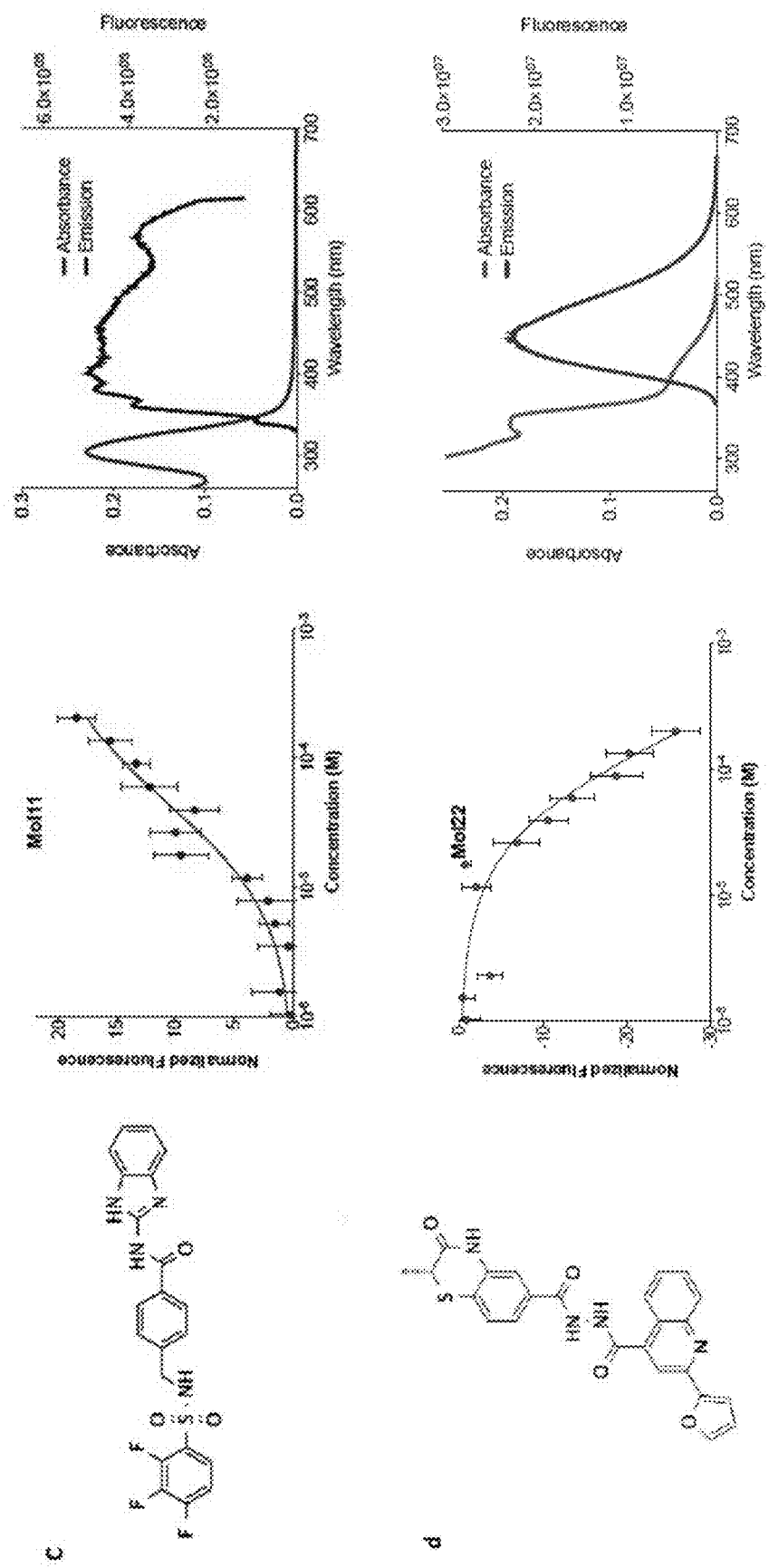
FIGURE 9C-D

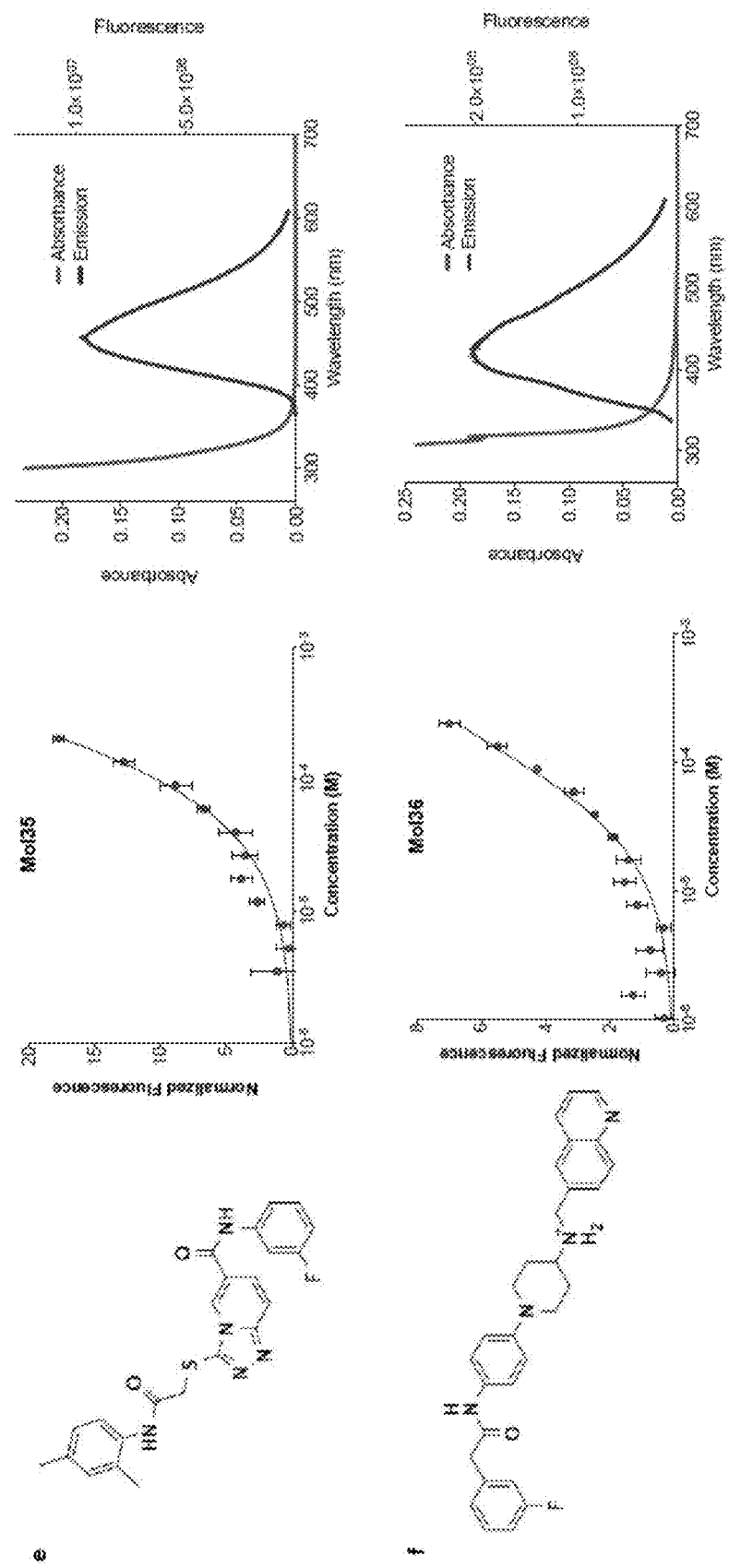
FIGURE 9E-F

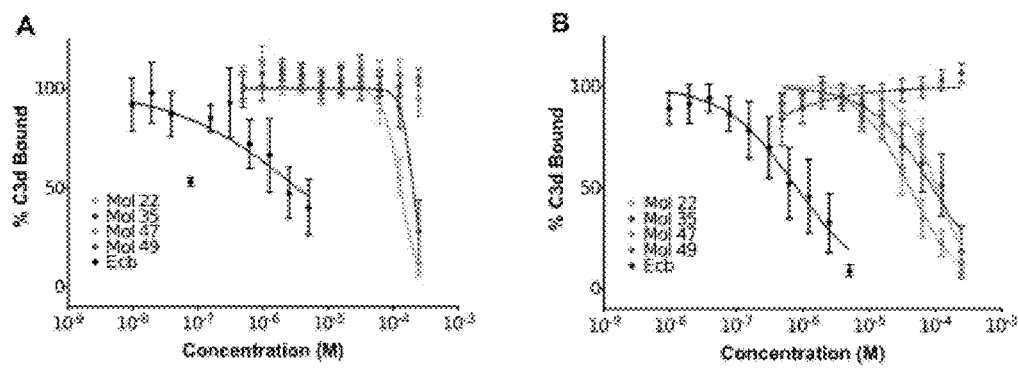
FIGURE 12A-B
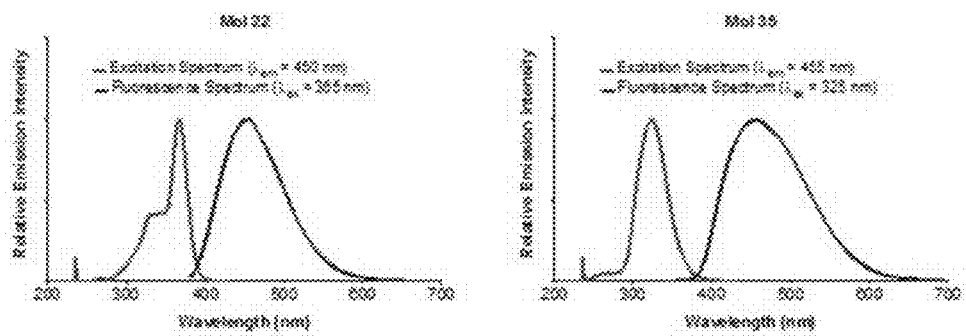
FIGURE 13

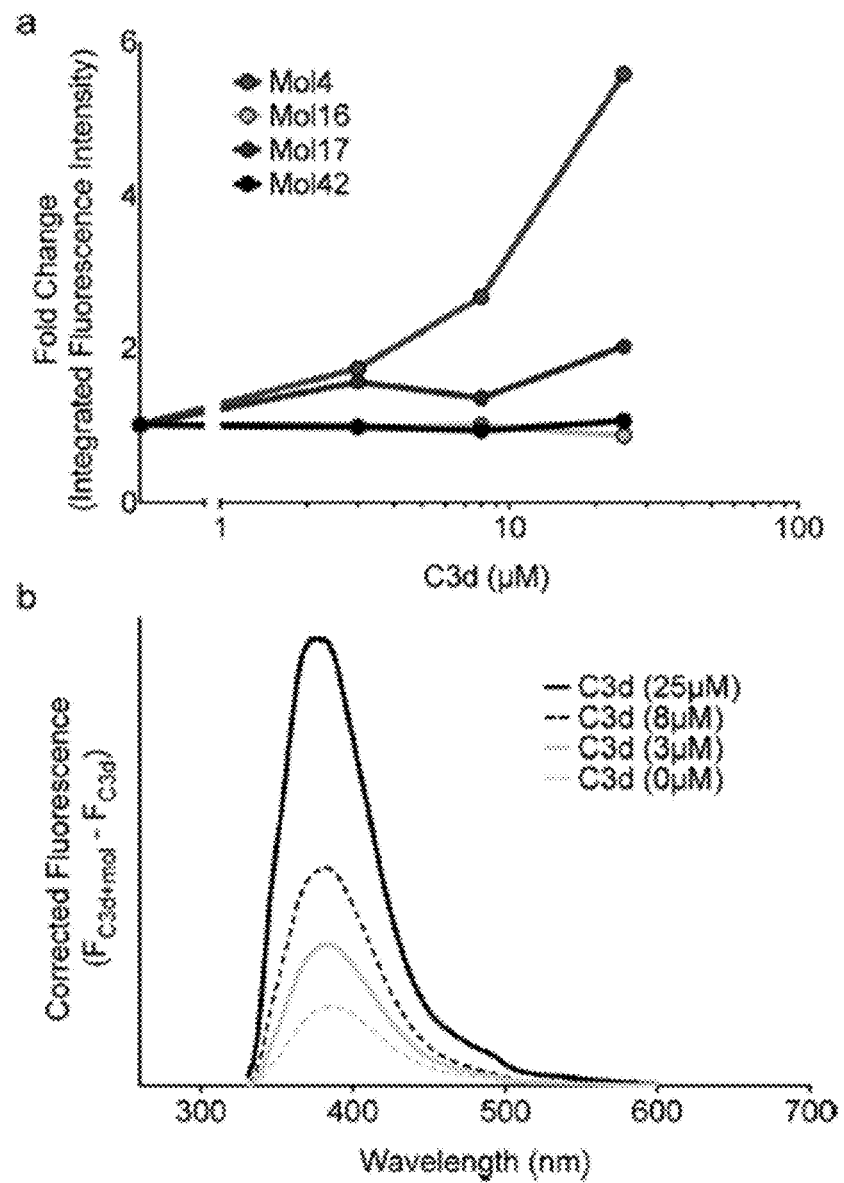
FIGURE 14A-B

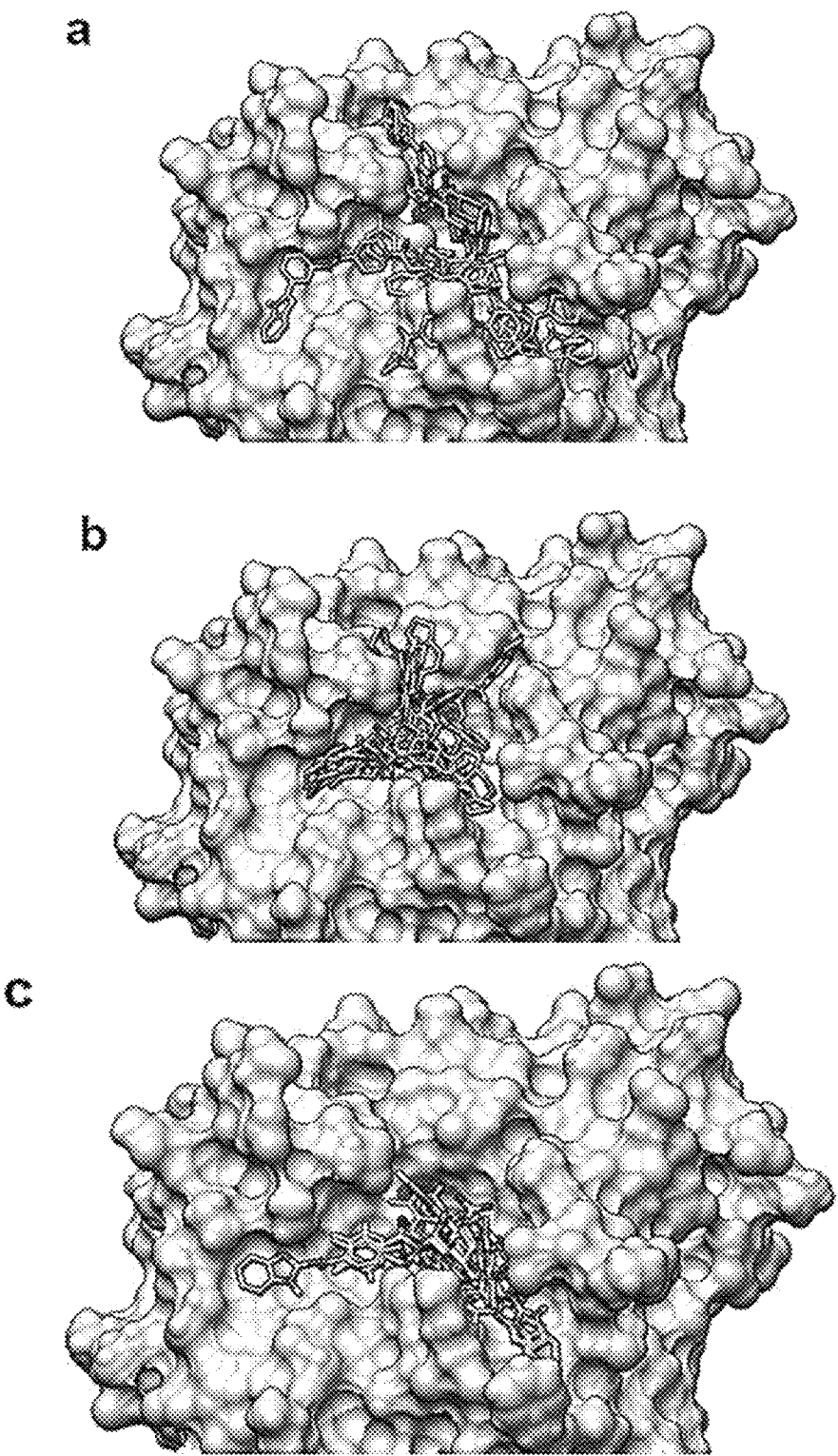
FIGURE 15A-C

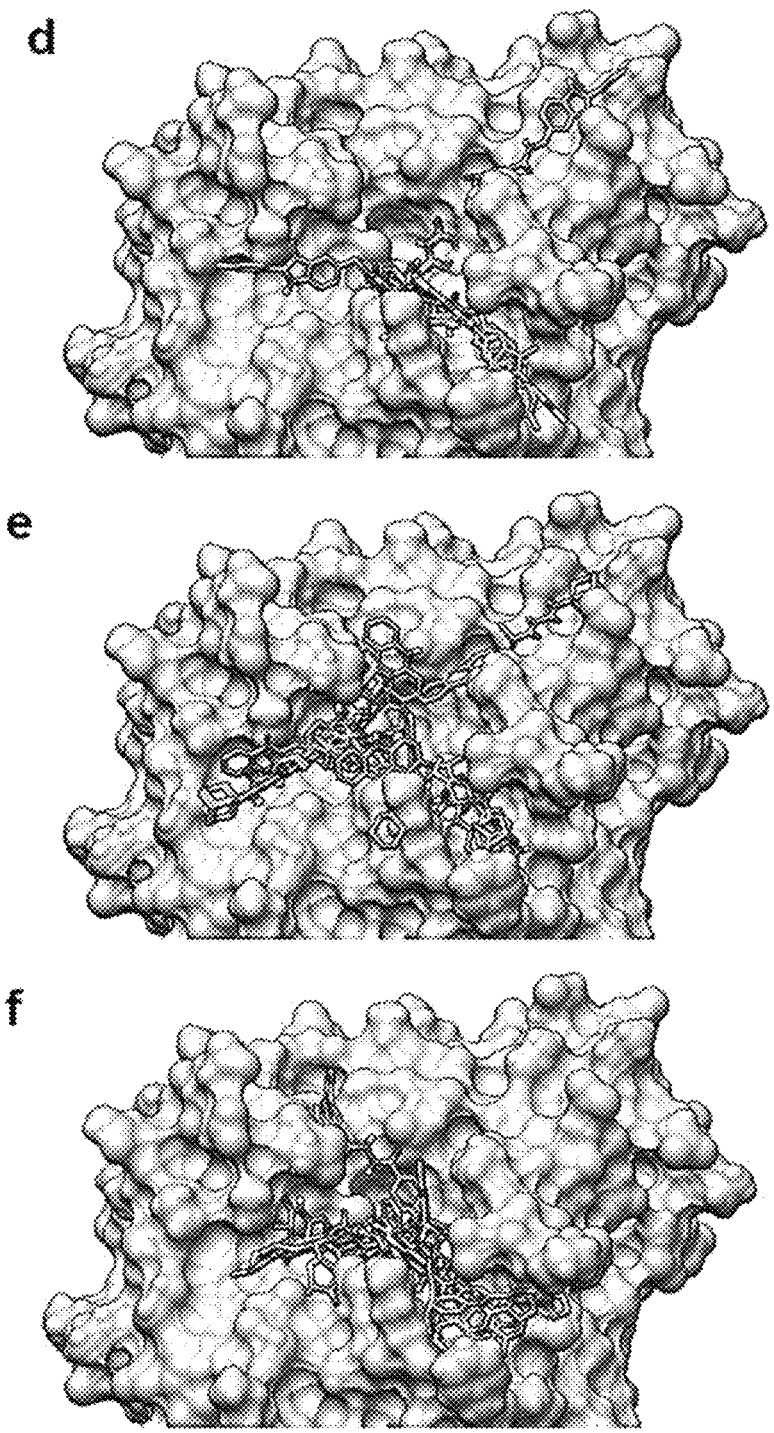
FIGURE 15D-F

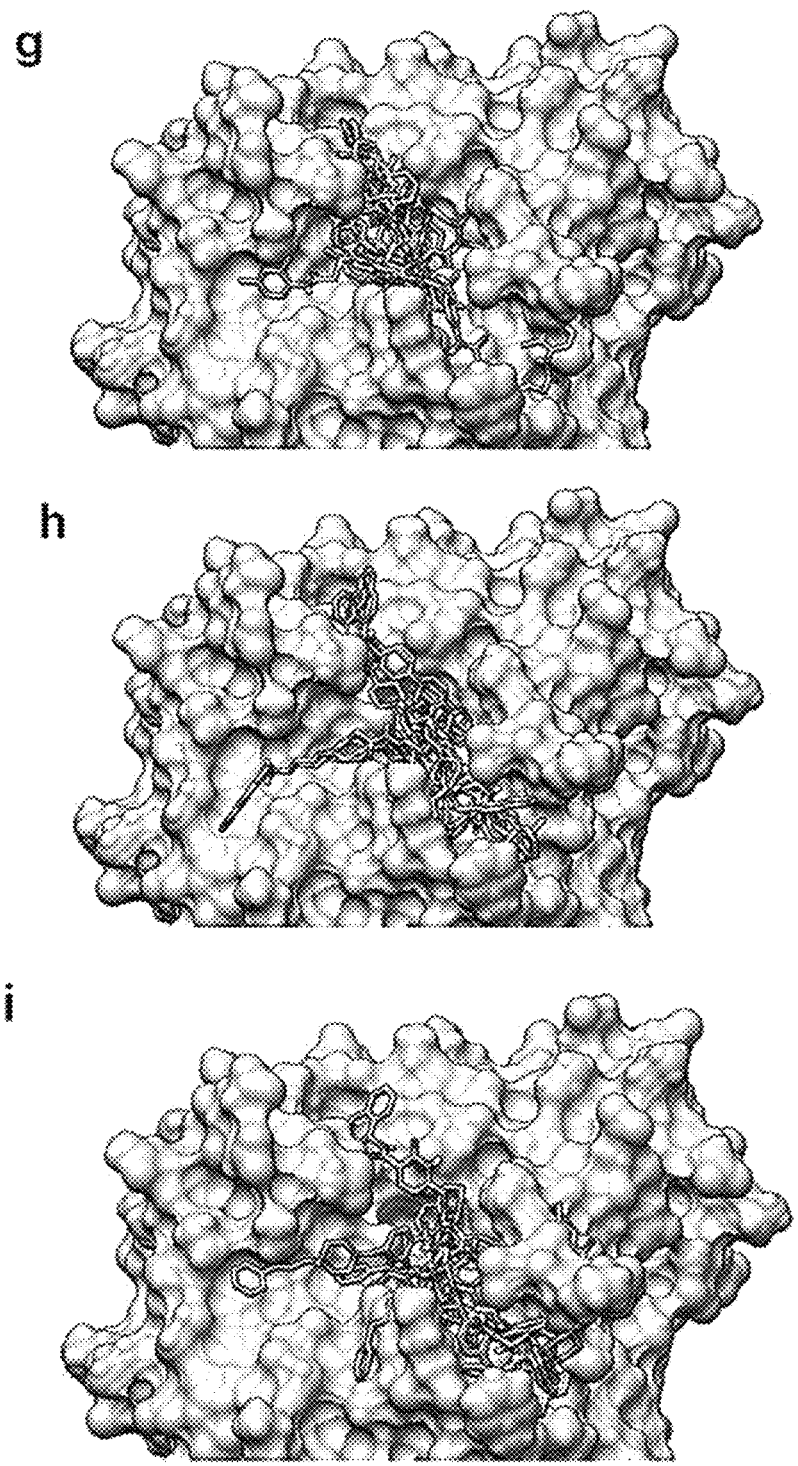
FIGURE 15G-I

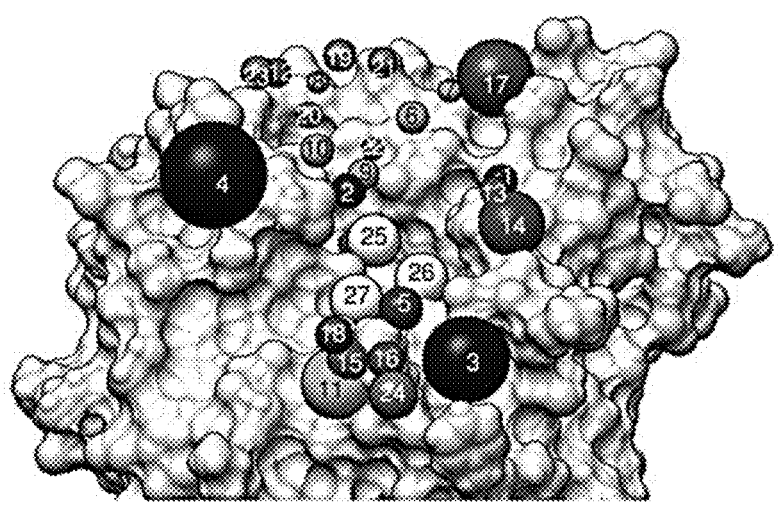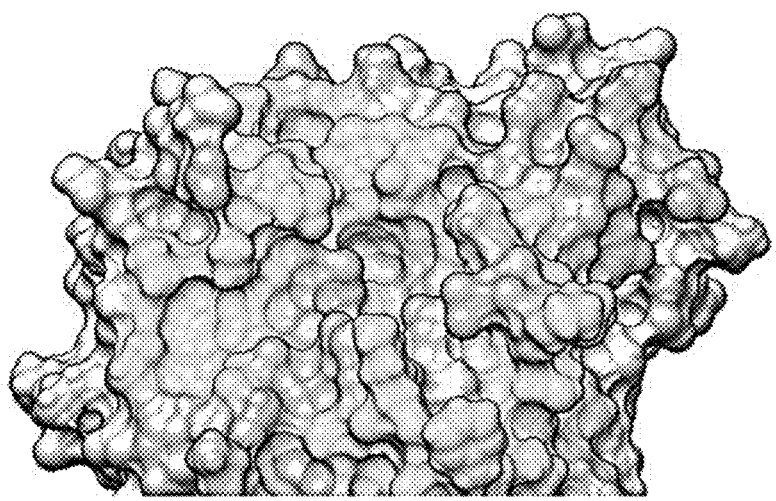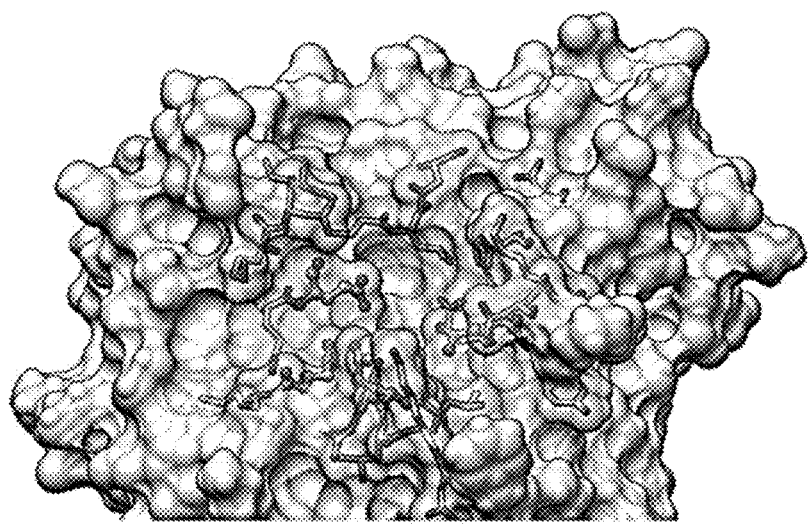
FIGURE 16A-C

US 10,259,824 B2

COMPLEMENT C3D-BINDING COMPOUNDS

CROSS REFERENCE TO RELATED APPLICATIONS

This application is a U.S. National Stage Application filed under 35 U.S.C. § 371 and claims priority to International Application No. PCT/US2016/030335, filed May 1, 2016, which application claims priority under 35 U.S.C. § 119 from Provisional Application Ser. No. 62/156,176, filed May 1, 2015, the disclosures of which are incorporated herein by reference.

TECHNICAL FIELD

The disclosure provides for compounds that bind with a high affinity to the C3d component of complement. The disclosure further provides for the use of the C3d-binding compounds as therapeutic and/or diagnostic agents for complement-mediated diseases or disorders.

BACKGROUND

The complement system is involved in progression of autoinflammatory diseases. Current treatments for such diseases involve inhibitors that block specific inflammation pathways, which often lead to systemic immunosuppression and susceptibility to infections. Targeting therapeutics to specific sites of inflammation holds promise for more efficient treatment, since lower concentration of drug would be required to achieve similar level of activity, and inflammation pathways would not be inhibited systemically, resulting in reduced immunosuppression.

SUMMARY

The disclosure provides for a pharmaceutical composition comprising a pharmaceutically acceptable excipient and/or diluent and a C3d-binding compound capable of complexing with complement component 3d (C3d) with a $K_d$ less than 100 µM, and wherein the compound is further characterized by comprising at least one of more of the following: 3 to 7 ring structures, wherein at least three of the ring structures are aromatic; at least 3 nitrogen atoms; at least 1 amide bond; and having a molecular weight less than about 600. In a further embodiment, the C3d-binding compound is capable of complexing with C3d with a $K_d$ less than 2 µM. In another embodiment, at least one of the 3 to 7 ring structures of the compound is heteroaromatic, the compound has at least four nitrogen atoms, and/or the compound has at least 2 amide bonds. In yet a further embodiment, the compound has fluorescence properties.

In one embodiment, the disclosure further provides for a pharmaceutical composition comprising a compound having a structure selected from:

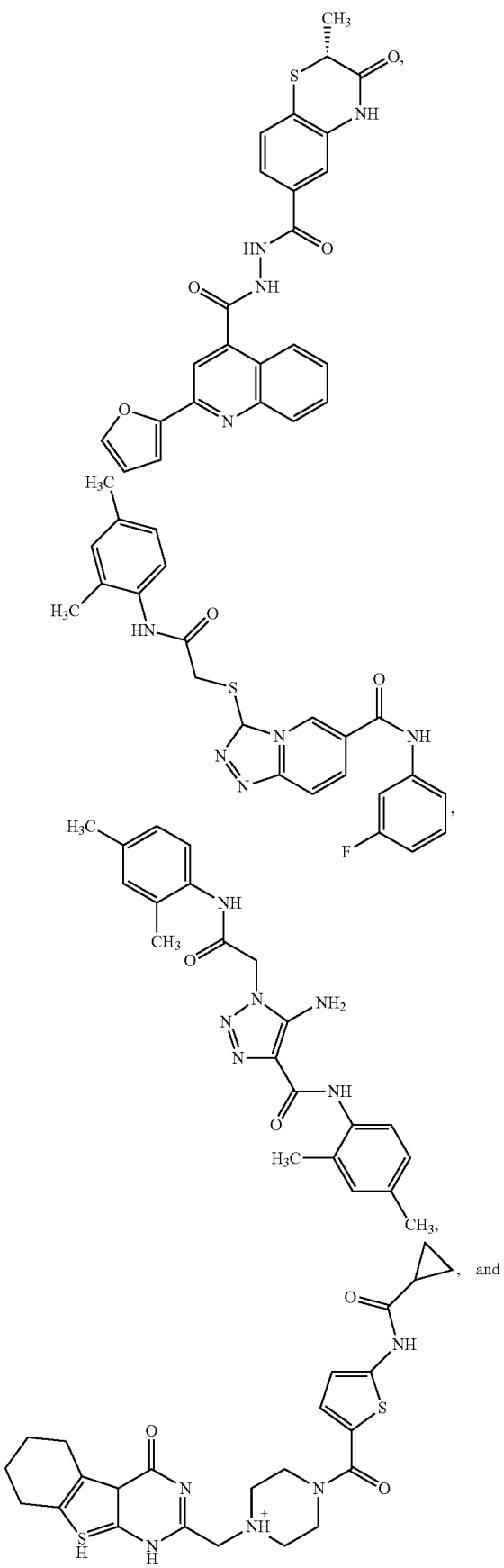

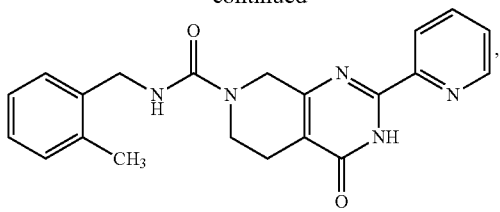

or a derivative of any one of the foregoing structures. In a further embodiment, the derivative has substantially the same structure as the parent compound but 1 to 4 of the functional groups have been modified or changed, wherein the derivative is further characterized by having increased binding affinity for C3d and/or improved fluorescence properties (e.g., exhibiting low quantum yield in its free (unbound) state, and undergoing a significant increase in quantum yield upon binding to C3d).

In a another embodiment, the disclosure provides for a pharmaceutical composition comprising a C3d-binding compound which is used to locate sites of complement activation, quantify the degree of complement activation, and to target therapeutic molecules to sites of complement-mediated inflammation.

In a particular embodiment, the disclosure provides a method of treating or diagnosing a complement-mediated disease or disorder in a subject, or the amelioration of the pathophysiology of diseases or disorders caused by the over activity of the complement system in subject, comprising administering a pharmaceutical composition comprising a C3d-binding compound disclosed herein. Examples of complement-mediated disease or disorders are selected from age-related macular degeneration, systemic lupus, rheumatoid arthritis, glomerulonephritis, psoriasis, asthma, Alzheimer's disease, Huntington's disease, Parkinson's disease, age-related macular degeneration, membranoproliferative glomerulonephritis Type 2, kidney disease, atypical hemolytic uremic syndrome, hereditary angioedema, accelerated atherosclerosis, periodontal disease and paroxysmal nocturnal hemoglobinuria. In another embodiment, the complement-mediated disease or disorder is age-related macular degeneration and wherein the compound further allows for localization of C3d in a subject's eye(s) by fluorescence. In yet another embodiment, the pharmaceutical composition is formulated for intravitreal injection, subtenon injection, or topical administration.

In yet another embodiment, the disclose further provides for a complement screening method to identify lead compounds comprising: identifying candidate compounds by pharmacophore screening for compounds that have chemical and geometric similarities to a ligand which binds to a complement component; simulating the docking by the candidate compounds to the complement component; simulating the dynamics of the candidate compounds-complement component interactions to account for receptor flexibility during docking; and scoring the candidate compounds comprising the following criteria: (i) ranking the candidate compounds based upon mean binding energies across all component conformations, (ii) identifying candidate compounds that docked in positions that overlapped with two or more pharmacophore features, and (iii) subjecting docked poses of the candidate compounds to RMSD-based clustering to identify candidate compounds with low-energy poses that bind in similar conformations to all complement component conformations; and identifying lead compounds by determining which candidate compounds exhibited the highest scoring across all criteria. In a further embodiment, the complement component is C3d, the ligand that binds to C3d is CR2, and the lead compound is a C3d-binding compound.

The disclosure also provides a method of diagnosing or detecting a complement mediated disease or disorder, comprising administering a pharmaceutical composition of any of claims 1-10 and measuring the binding of the C3d-binding compound to C3d by detecting fluorescence wherein a localized increase in fluorescence in indicative of the complement mediated disease or disorder.

The disclosure also provides a C3d-binding compound selected from:

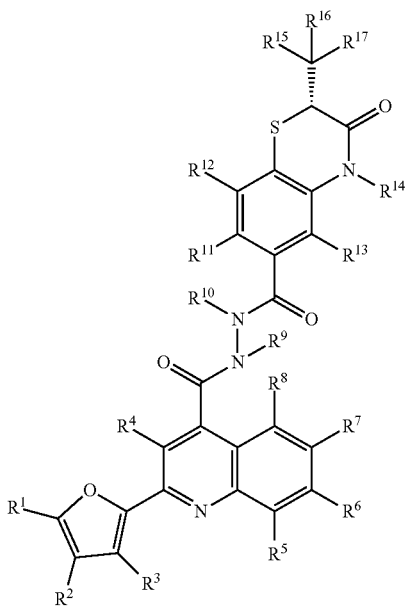

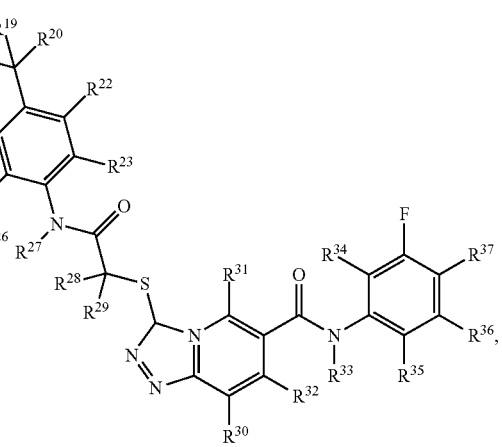

-continued

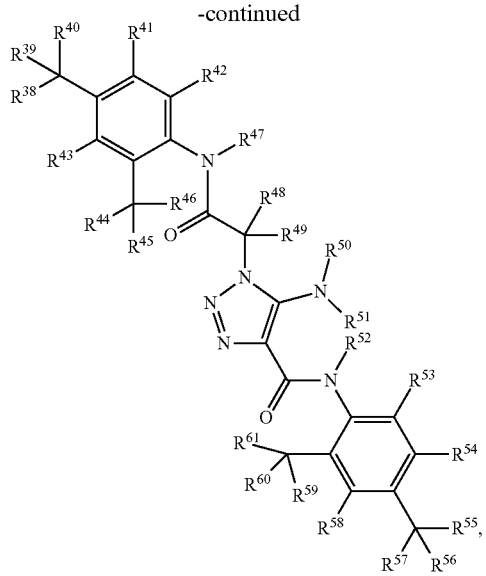

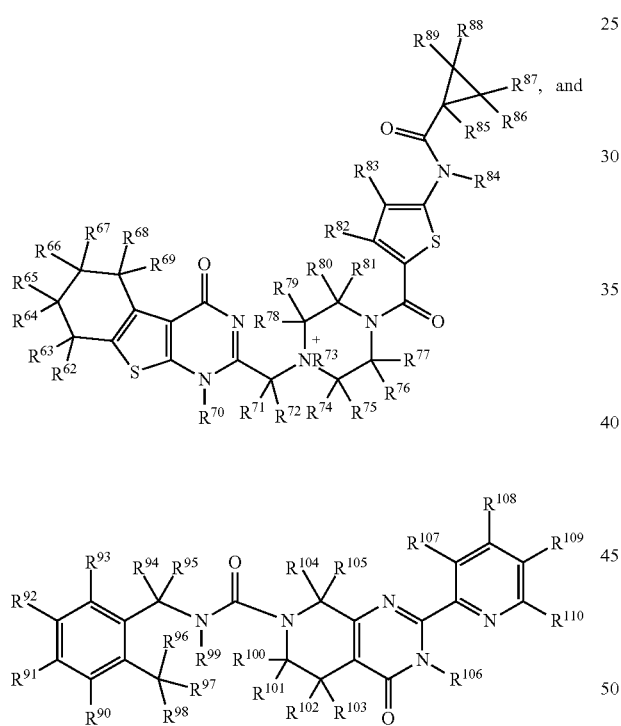

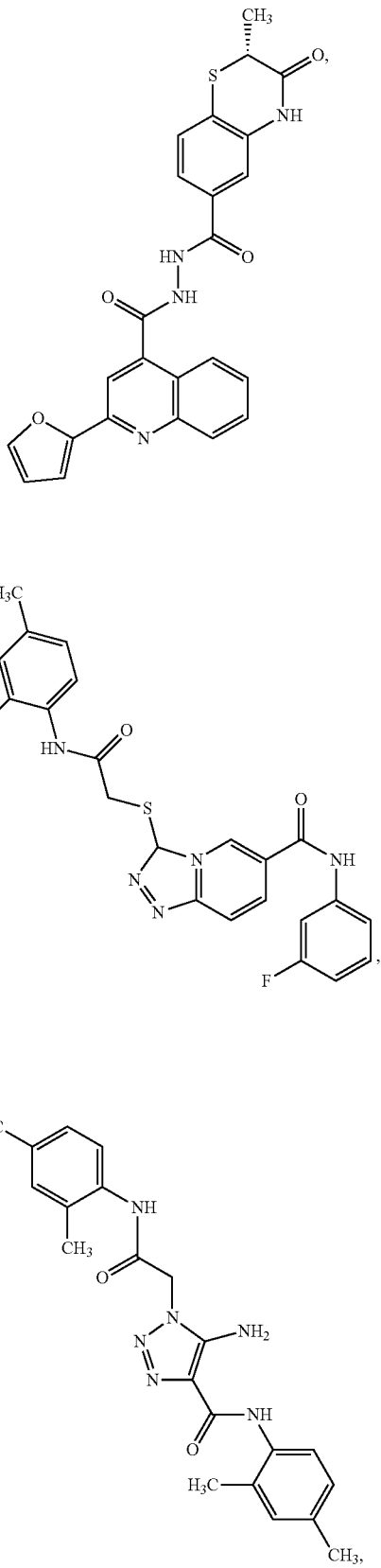

wherein, $R^1$-$R^{110}$ is independently selected from H, D, optionally substituted $(C_1$-$C_6)$alkyl, optionally substituted hetero-$(C_1$-$C_6)$alkyl, optionally substituted $(C_1$-$C_6)$alkenyl, optionally substituted hetero-$(C_1$-$C_6)$alkenyl, optionally substituted $(C_1$-$C_6)$alkynyl, optionally substituted hetero-$(C_1$-$C_6)$alkynyl, optionally substituted $(C_1$-$C_6)$cycloalkyl, optionally substituted $(C_1$-$C_6)$cycloalkenyl, optionally substituted aryl, optionally substituted heterocycle, hydroxyl, halo, imine, amine, amide, nitro, nitroso, nitrile, isocyanate, alkoxide, ester, carbonyl, carboxyl, thiol, SH, $SR^1$, thionyl, sulfonyl, $SiR^1_3$, $PR^1_3$, and heterocycle. In one embodiment, the Cd3-binding compound of claim 18, wherein the compound is selected form the group consisting of:

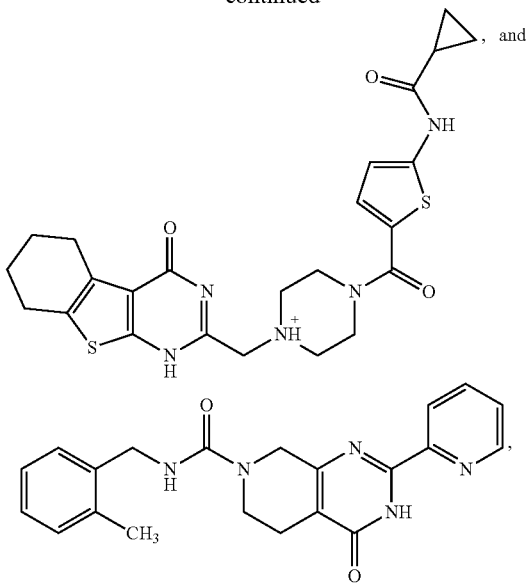

or a derivate of anyone of the foregoing structures.

DESCRIPTION OF DRAWINGS

FIG. 7A-D shows the dependence of molecule fluorescence quantum yield on solvent viscosity and polarity. The quantum yield of Mol16 is highly correlated with solvent viscosity (A), but not with polarity (B). Conversely, the quantum yield of Mol42 is not correlated to solvent viscosity (C), but is inversely related to solvent polarity (D).

FIG. 8A-B presents the chemical structure (A) and concentration-dependent thermophoresis binding curve (B) for top C3d-binding molecule from second iteration of virtual screening.

FIG. 9A-F provides chemical structures, binding, and fluorescence data for other six molecules from vHTS. Data is shown for Mol1 (A), Mol 5 (B), Mol11 (C), Mol22 (D), Mol35 (E), and Mol42 (F). Chemical structures are shown in the left panels, concentration-dependent thermophoresis binding curves in the center panels, and absorption and emission spectra in the right panels.

FIG. 12A-B presents competitive binding ELISA data, showing inhibition of C3d-CR2 (A) and C3d-Ecb (B) interactions by lead compounds Mol 22 (cyan), 35 (blue), and 47 (magenta). Ecb (black) and Mol 49 (purple) were used as positive and negative controls, respectively.

FIG. 13 presents excitation and fluorescence emission spectra of Mol 22 (left) and 35 (right).

FIG. 14A-B shows Fluorescence of top-performing molecules in the presence of C3d. (A) The fold-change in integrated fluorescence emission intensity is shown as a function of C3d concentration for Mol4, -16, -17, and -42. The fold change is the ratio of integrated fluorescence emission intensity at each C3d concentration to that of the molecule alone (0 µM C3d). (B) Corrected fluorescence emission spectra of Mol4 in the presence of 0, 3, 8, and 25 µM C3d.

FIG. 15A-J shows docked poses of ten C3d-binding molecules to C3d. The molecules represent the top ten low-energy binding poses of each molecule. (a) Mol4, (b) Mol5, (c) Mol11, (d) Mol16, (e) Mol17, (f) Mol22, (g) Mol35, (h) Mol36, (i) Mol42, (j) Mol68.

FIG. 16A-C shows conserved binding sites of docked poses of C3d-binding molecules. (A) Original 27 pharmacophore features using in vHTS. (B) Binding site residues of C3d in contact with docked poses of ligands. Residues involved in contacts with >50, 11-50, and 1-10 docked ligand poses are different gray-scale on the C3d surface. (C) C3d residues involved in hydrogen bonds with docked ligand poses. Residues involved in >10, 5-9, and 1-5 hydrogen bonds with docked ligand poses are different gray-scale on the C3d surface.

DETAILED DESCRIPTION

Figure 1:
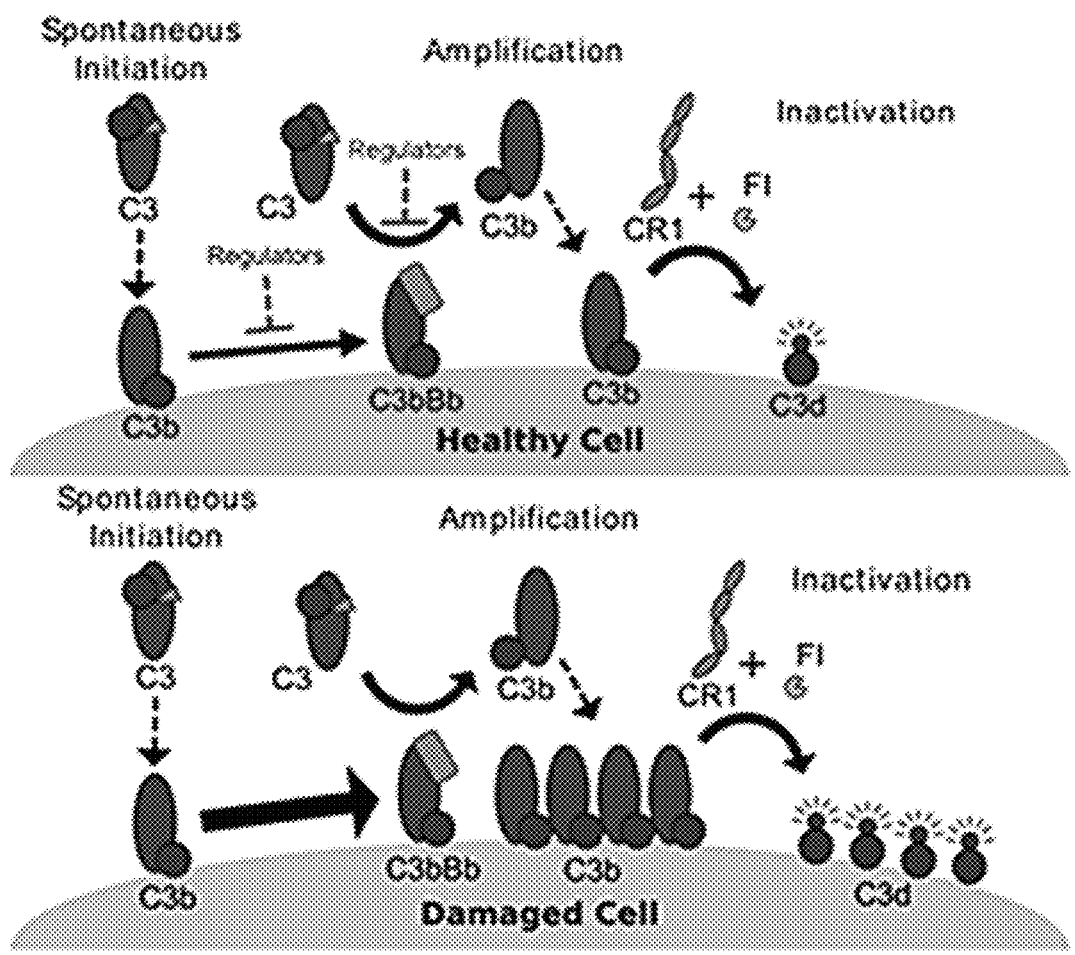
FIG. 1 presents an overview of complement activation and regulation on healthy and damaged cells. Complement is continuously activated at low levels, leading to production of active fragment C3b, which can covalently attach to cell surfaces via the C3d domain (dark blue circle). Under normal conditions, complement regulators prevent further cleavage of C3 to C3b by convertase enzymes (C3bBb), and eventually inactivate cell-bound C3b molecules by cleavage to C3d. When complement is dysregulated or under inflammatory conditions, C3b is rapidly amplified on cell surfaces, and subsequent C3b cleavage events lead to an accumulation of C3d, the long-lived biomarker of complement activation. The red beacon attached to C3d symbolizes fluorescent small molecules that can detect sites of complement-mediated inflammation.

As used herein and in the appended claims, the singular forms "a," "and," and "the" include plural referents unless the context clearly dictates otherwise. Thus, for example, reference to "a probe" includes a plurality of such cells and reference to "the cell" includes reference to one or more cells and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. With respect to any term that is presented in one or more publications that is similar to, or identical with, a term that has been expressly defined in this disclosure, the definition of the term as expressly provided in this disclosure will control in all respects.

Complement activation produces a terminal cleavage product known as C3d, which covalently attaches to cell surfaces and acts as a biomarker for autoinflammation. Recent work has aimed at using C3d as a target to monitor spatiotemporal disease progression and to deliver therapeutics to affected sites. Specifically, attempts have been made to develop noninvasive methods to detect C3d in vivo, using magnetic resonance imaging of C3d-targeted iron oxide nanoparticles and fluorescence imaging of monoclonal antibodies, respectively. While these attempts represent significant advances, it would be beneficial to formulate C3d diagnostics using non-protein chemical compounds. Small chemical compounds offer many advantages in context of molecular diagnostics and therapeutics. They have higher bioavailability than larger protein-based therapeutics, are less prone to degradation, and are more cost effective to produce. Since most complement-targeted therapeutics are proteins, development of small molecules represents a major step forward. Furthermore, many protein-protein interactions in complement have relatively weak binding affinities, thus development of high-affinity molecules can compete easily with these interactions. Provided herein are small chemical compounds that can bind to the complement protein C3d with high affinity. The C3d-binding compounds were discovered through in silico virtual high-throughput screening, and validated through direct and competitive binding experiments. The C3d-binding compounds can be used as therapeutic agents for monitoring and treating a wide array of complement-mediated diseases.

For the purposes of this disclosure, "small molecule" refers to organic compound that is of low molecular weight (e.g., <900 daltons, preferably <500 daltons) with a size on the order of $10^{-9}$ m. Accordingly, a "small molecule" as used herein does not include proteins.

Autoimmune diseases are a primary cause of chronic inflammation. Recent breakthroughs have led to treatments that target factors involved in disease progression. For systemic diseases, this typically results in immunosuppression, which leaves patients highly susceptible to infection. Furthermore, this type of treatment is often inefficient, requiring large doses of therapeutics to achieve a desired outcome. Recent efforts have focused on targeting therapeutics to particular sites of inflammation. This approach requires knowledge of where tissue damage occurs.

Many autoimmune diseases are characterized by altered levels of specific molecules (biomarkers), which are helpful in diagnosis, tracking disease progression, and locating the affected region in the body. These biomarkers can provide spatiotemporal information that can assist clinicians in treating disease. Therefore, it is highly desirable to develop methods for noninvasive detection of biomarkers, which can enable evaluation of disease progression in vivo, and can be used for targeting therapeutics at the appropriate place and time.

The complement system plays a role in many autoimmune and inflammatory diseases. Complement is considered a double-edged sword; it has evolved the capability to rapidly detect and eliminate pathogens, but relies on coordination of complement regulator proteins to confer protection against host cell and tissue damage. Involvement of complement in autoinflammatory diseases stems from improper complement activation, dysregulation, or deficiency. For example, mutations in complement regulator factor H leads to reduced complement regulation, and increases in the likelihood of developing both age-related macular degeneration and atypical hemolytic uremic syndrome. Alternatively, generation of autoantibodies (antibodies against self-antigens) and inadequate clearance of immune complexes result in classical pathway complement activation, which further exacerbates chronic inflammation resulting from these autoimmune diseases.

Excessive and inappropriate complement activation often plays an integral role in the development and progression of autoinflammatory conditions. Many recent efforts have focused on development of complement-targeted therapeutics and diagnostics, which can effectively regulate and detect complement-mediated inflammation. Indeed, two therapeutics are currently on the market for treatment of complement-related diseases, and many more are in the pipeline. Additionally, fluorescently-labeled monoclonal antibodies are being developed for in vivo detection of complement-mediated inflammation. However, the majority of these molecules are biopharmaceuticals, which are expensive to produce, difficult to deliver, and exhibit poor in vivo stability and bioavailability. It is desirable to identify small drug-like complement diagnostic and therapeutic molecules to overcome these challenges. While complement activation is dependent on enzymatic cleavage of complement components, propagation of the cascades rely primarily on large protein complexes, which are comprised of expansive and topographically flat interfaces that lack defined cavities for small molecule binding. As a consequence, few small molecules that bind or inhibit complement have been identified, and all of these bind to enzyme active sites or GPCRs, which represent traditional targets for small drug-like chemical compounds.

Since complement is involved in most autoinflammatory diseases, levels of complement proteins (both precursors and activation products) are often correlated with disease states. Measurement of serum levels of complement factors, however, often leads to misdiagnoses, since serum levels are highly variable in both healthy and diseased individuals. Since complement activation is characterized by extensive covalent attachment of proteins to cell surfaces, a more reliable alternative involves measurement of complement activation products on affected tissues (see FIG. 1). During complement activation, complement component 3 (C3) is cleaved, exposing a reactive thioester that can covalently link nascently-generated C3b to cell surfaces. Further cleavage events yield C3d (the terminal cleavage product of C3), which remains covalently linked to cells long after complement activation, and has been explored and used for tracking disease progression in a number of conditions, including neurological (Alzheimer's disease and multiple sclerosis), renal (kidney disease, lupus nephritis, glomerulonephritis, membranoproliferative glomerulonephritis Type 2 (a.k.a. dense deposit disease), paroxysmal nocturnal hemoglobinuria and atypical hemolytic uremic syndrome), ocular (age-related macular degeneration), and systemic (systemic lupus erythematosus, rheumatoid arthritis, and chronic obstructive pulmonary disease) diseases, and xenotransplantation. However, measurement of C3d levels typically requires tissue biopsies. It is therefore desirable to develop a noninvasive method to detect levels of complement activation fragments on tissues.

C3d is a marker for complement activation, but also functions to stimulate B cell activation and production of antibodies through its interaction with complement receptor 2 (CR2). Indeed, several studies have shown that molecular therapeutic agents (e.g., soluble complement regulators or antibodies that downregulate complement activation) targeting sites of complement activation (i.e., where C3d has been deposited) via CR2 can locally inhibit complement activation, resulting in a more efficient therapeutic, while simultaneously minimizing susceptibility to infections. Small chemical compounds offer many advantages in context of molecular diagnostics and therapeutics. They have higher bioavailability than larger protein-based therapeutics, are less prone to degradation, and are more cost effective to produce. Since most complement-targeted molecules are proteins, development of small molecules represents a major step forward.

The disclosure provides for the identification of small molecules capable of binding to C3d. In identifying these C3d-targeted molecules, a comprehensive virtual high-throughput screening (vHTS) protocol was used to search over seven million drug-like small molecules for predicted binding to C3d. Experimental binding studies led to the identification of 11 molecules that bind to C3d, with affinities ranging from 1-500 µM. In contrast to other complement therapeutics and binding agents, the C3d-binding compounds disclosed herein bind to non-traditional drug targets (enzymes and GPCRs) of complement. C3d is a terminal cleavage product of C3, produced during complement activation, which covalently attaches to cell surfaces. In many inflammatory disorders, complement is activated on host cells and tissues, thus C3d can act as a long-lived biomarker of complement activation. In certain embodiments, the C3d-binding compounds disclosed herein can be utilized to locate sites of complement activation, quantify the degree of complement activation, and to target therapeutic molecules to sites of complement-mediated inflammation. In further embodiments, the disclosure provides for the use of the C3d-binding compounds as a therapeutic for the treatment of complement-mediated diseases or disorders, or for the amelioration of the pathophysiology of diseases or disorders caused by the over activity of the complement system. Examples of such complement-mediated diseases or disorders include, but are not limited to, autoimmune diseases, such as systemic lupus, rheumatoid arthritis, glomerulonephritis, and psoriasis; inflammatory diseases, such as asthma; and neurodegenerative diseases, such as Alzheimer's disease (particularly Alzheimer's disease in a subject carrying an ApoE4 allele, i.e. a subject who is heterozygous or homozygous for the ApoE4 allele), Huntington's disease, Parkinson's disease; age-related macular degeneration; membranoproliferative glomerulonephritis Type 2; atypical hemolytic uremic syndrome; hereditary angioedema; atherosclerosis (in particular, accelerated atherosclerosis); and paroxysmal nocturnal hemoglobinuria. "Overactivity of the complement system" refers to hyperactivity of the complement system which results in "bystander" damage to healthy cells and tissue, and in some cases severe damage.

Accordingly, the disclosure provides methods that can be used to identify and diagnose inflammatory disease and disorders of the mucosa (e.g., mouth, nose, vagina etc.) as well as disease such as neurological disease (Alzheimer's disease and multiple sclerosis), renal (kidney disease, lupus nephritis, glomerulonephritis, membranoproliferative glomerulonephritis Type 2 (a.k.a. dense deposit disease), paroxysmal nocturnal hemoglobinuria and atypical hemolytic uremic syndrome), ocular (age-related macular degeneration), and systemic (systemic lupus erythematosus, rheumatoid arthritis, and chronic obstructive pulmonary disease) diseases, and xenotransplantation.

In some embodiments disclosed herein, the subject is a human subject. However, it may alternatively be desired to ameliorate, treat, or prevent (or diagnose or monitor progression of) the disease in non-human animals, such as domestic pets.

It has been found that some of the C3d-binding compounds are strongly fluorescent, exhibiting emission quantum yields ($\Phi_{fl}$) larger than 0.2. Additionally, one compounded exhibited a five-fold enhancement in fluorescence upon an increase in the viscosity of the immediate environment. Thus, as many of the identified C3d-binding compounds are fluorescent, the disclosure further provides for the use of C3d-binding compounds as diagnostic agents for the detection and treatment of complement-mediated inflammation in vivo. For example, the compounds of the disclosure can be used to detect C3d in various portions of the body, in particular the eye. For example, the C3d-binding compounds disclosed herein are ideally suited for not only visualizing the localization of C3d in an eye, but also can potentially inhibit its action. Accordingly, in some embodiments, the C3d-binding compounds of the disclosure can assess the risk of over reactivity of the complement system by visualizing C3d. In further embodiments, the C3d-binding compounds also inhibit C3d from exerting its normal activity. Of particular interest for such dual action activities (i.e., diagnostic and therapeutic) by the C3d-binding compounds is the use of the compounds in subjects who may have age-related macular degeneration (AMD). AMD is one of the most well-characterized late-onset, complex trait diseases. AMD which affects approximately 5% of persons older than age 75 years is among the most debilitating of chronic human diseases. Given that age is the primary risk factor for AMD, the prevalence and severity of the condition are predicted to increase as human life expectancy increases. Accordingly, the C3d-binding compounds can be administered to the eyes of a subject suspected of having AMD to diagnosis whether the subject has the onset of the disease. Additionally, the C3d-binding compounds can be administered to treat a subject who has AMD. Examples of such administration include formulating the C3d-binding compounds for intravitreal injection, subtenon injection, or topical administration (e.g., drops, emulsions, suspensions, ointment and gels).

In a particular embodiment, the disclosure provides for C3d-binding compounds that are small molecules capable of complexing with C3d. In a further embodiment the C3d-binding compounds can complex with C3d with a $K_d$ less than 450 μM. In yet a further embodiment, the C3d-binding compound is characterized by having one or more of the following characteristics: 3 to 7 ring structures; at least 3 nitrogen atoms; at least 1 amide bond; and having a molecular weight less than about 600. In another embodiment, the C3d-binding compounds can complex with C3d with a $K_d$ less than 1 μM. In yet another embodiment, the C3d-binding compounds can complex with C3d with a $K_d$ from 1 nM to 500 nM. In a certain embodiment, at least one or more of the ring structures is heteroaromatic.

In a particular embodiment, the C3d-binding compound is selected from:

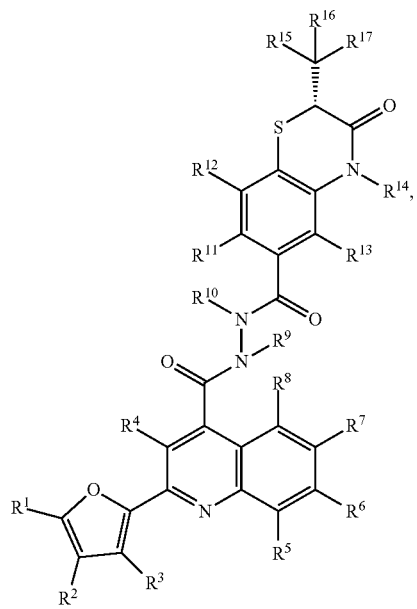

-continued

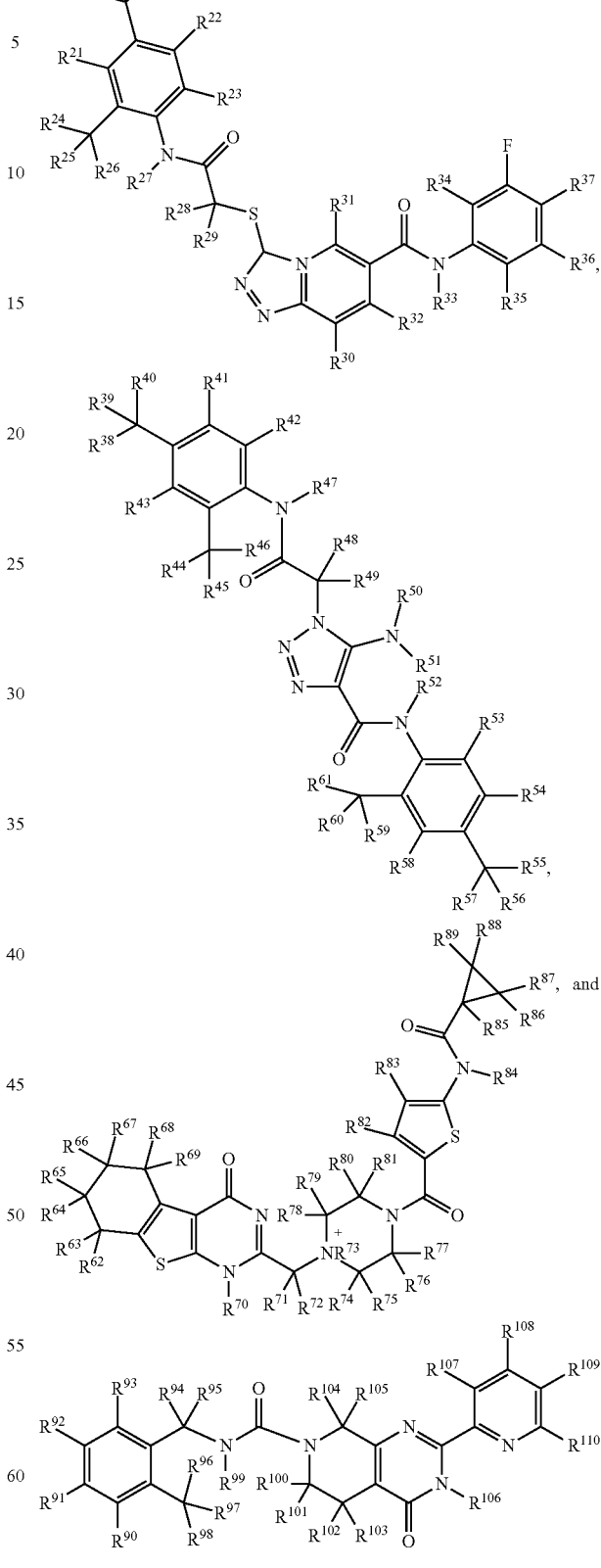

wherein,
$R^1$-$R^{110}$ is independently selected from H, D, optionally substituted ($C_1$-$C_6$)alkyl (e.g., $CF_3$), optionally substituted hetero-$(C_1-C_6)$alkyl, optionally substituted $(C_1-C_6)$alkenyl, optionally substituted hetero-$(C_1-C_6)$alkenyl, optionally substituted $(C_1-C_6)$alkynyl, optionally substituted hetero-$(C_1-C_6)$alkynyl, optionally substituted $(C_1-C_6)$cycloalkyl, optionally substituted $(C_1-C_6)$cycloalkenyl, optionally substituted aryl, optionally substituted heterocycle, hydroxyl, halo (e.g., F, Cl, Br, or I), imine, amine (e.g., $NH_2$ or $NR^1_2$), amide, nitro, nitroso, nitrile, isocyanate, alkoxide (e.g., O-alkyl or O-ether), ester, carbonyl (e.g., aldehyde, or ketone), carboxyl, thiol, SH, $SR^1$, thionyl, sulfonyl, $SiR^1_3$, $PR^1_3$, and heterocycle (e.g., pyridine, triazole, pyrimidine, or pyrazine). In a further embodiment, the disclosure provides for derivatives of any of the foregoing structures by replacing, removing or adding 1 to 5, 1 to 4, 1 to 3, or 1 to 2 functional groups (including ring structures), wherein the derivative substantially has the same structure as the parent but has increased binding affinity for C3d and/or improved fluorescence properties (e.g., exhibiting low quantum yield in its free (unbound) state, and undergoing a significant increase in quantum yield upon binding to C3d).

Further, the disclosure provides screening methods that can be used to successfully identify small molecules that bind to complement. Moreover, the methods are generally applicable and can be used to identify agents that can bind to specific components of complement. These agents can be targeted for detection and/or inhibition. In a particular embodiment, the disclosure comprises a complement screening method to identify lead compounds, the method comprising: identifying candidate compounds by pharmacophore screening for compounds that have chemical and geometric similarities to a ligand which binds to a complement component; simulating the docking by the candidate compounds to the complement component; simulating the dynamics of the candidate compounds-complement component interactions to account for receptor flexibility during docking; and scoring the candidate compounds comprising the following criteria: (i) ranking the candidate compounds based upon mean binding energies across all component conformations, (ii) identifying candidate compounds that docked in positions that overlapped with two or more pharmacophore features, and (iii) subjecting docked poses of the candidate compounds to RMSD-based clustering to identify candidate compounds with low-energy poses that bind in similar conformations to all complement component conformations; and identifying lead compounds by determining which candidate compounds exhibited the highest scoring across all criteria.

The C3d-binding compounds described herein provide a foundation for the development of small molecule diagnostics of complement-mediated inflammation. In addition to binding to C3d, many of these molecules exhibit intrinsic fluorescent properties. By determining the molecule binding mode, either via extensive molecular dynamics simulations, NMR, or optimally crystallographic structures of C3d-ligand complexes, will allow for fine tuning of the structures of the C3d-binding compounds herein so as to provide even greater binding affinities. It is desirable for molecules to undergo a significant increase in quantum yield upon C3d binding. Indeed, a C3d-binding compound disclosed herein demonstrated a viscosity-dependent increase in quantum yield, indicating that as conformational freedom of the molecule is reduced, fluorescence intensity increases. This result suggests that the compound may exhibit stronger fluorescence emission in its C3d-bound state relative to its unbound state. It is possible to utilize chemical features of this molecule, in conjunction with knowledge of which chemical groups interact with C3d, to generate derivatives with more desirable binding and photophysical properties.

The disclosure further provides for pharmaceutical compositions comprising one or more C3d-binding compounds disclosed herein. Depending on the mode of administration, the pharmaceutical compositions can contain various pharmaceutically acceptable components, such as excipients, diluents, binders, disintegrants, etc.

Pharmaceutical compositions comprising the C3d-binding compounds may be prepared for administration orally, parenterally, transocularly, intranasally, transdermally, transmucosally, by inhalation spray, vaginally, rectally, into the cerebral spinal fluid, or by intracranial injection. The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and or surgical implantation at a particular site is contemplated as well. Generally, compositions for administration by any of the above methods are essentially free of pyrogens, as well as other impurities that could be harmful to the recipient. Further, the compositions for administration parenterally are sterile.

Direct intracranial injection or injection into the cerebrospinal fluid also can be used to introduce an effective amount of a C3d-binding compound. The C3d-binding compound may be combined with other therapeutic agents as described herein.

Intravascular infusions are normally carried out with the parenteral solution contained within an infusion bag or bottle or within an electrically operated infusion syringe. The solution may be delivered from the infusion bag or bottle to the subject by gravity feed or by the use of an infusion pump. The use of gravity feed infusion systems in some instances does not afford sufficient control over the rate of administration of the parenteral solution and, therefore, the use of an infusion pump may be desirable especially with solutions containing relatively high concentrations of spin trap/thrombolytic formulation. An electrically operated infusion syringe may offer even greater control over the rate of administration.

For treatment of neural damage associated with, for example, Alzheimer's disease, an appropriate daily systemic dosage of a C3d-binding compound formulation is based on the body weight of the subject and is in the range of from about 0.1 µg/kg to about 100 mg/kg, although dosages from about 0.1 mg/kg to about 100 mg/kg, or from about 0.5 mg/kg to about 20 mg/kg are also contemplated. Thus, for the typical 70 kg human, a systemic dosage can be between about 7 µg and about 7,000 mg daily. A daily dosage of locally administered material will be about an order of magnitude less than the systemic dosage. Oral administration is also contemplated.

In one embodiment, the C3d-binding compound may be administered chronically or continuously over a period of time to a subject that may be at risk of developing a complement-mediated disease or disorder. The route and formulation for administration may differ depending upon chronic or acute treatments.

In one embodiment, the C3d-binding compound may be administered in combination with one or more additional agents useful for treating a complement-mediated disease or disorder.

In chronic conditions (e.g., Alzheimer's disease), sustained or controlled release formulations are applicable. In acute conditions (e.g., overactivity of the complement system) an immediate release formulation is appropriate such as through IV delivery (or other parenteral delivery), local cerebral delivery and the like. In some embodiments, the C3d-binding compound composition is a delayed or controlled release dosage form that provides a $C_{max}$ of the C3d-binding compound that is at least about 35%, 40%, 45%, 50%, 55%, 60%, 65%, 70%, 75%, 80%, 85%, or 100% higher than the $C_{max}$ provided by an immediate release dosage form containing the same amount of the C3d-binding compound. In some embodiments, the $C_{max}$ is up to about 75%, 100%, 125% or 150% higher than the $C_{max}$ of the immediate release dosage form. $C_{max}$ refers to the maximum dose of the C3d-binding compound in the blood after dosing and provides an indicator that the drug is absorbed systemically.

In some embodiments, the AUC of the delayed or controlled release dosage form is also increased by at least about 20%, 25%, 30%, 35%, 40%, 45%, or 50%, or up to about 50%, 60%, 75% or 100% relative to an immediate release dosage form. AUC or "area under the curve", and refers to the kinetic curve derived when plasma drug concentration versus time is measured after dosing of a drug.

The preparation of delayed, controlled or sustained/extended release forms of pharmaceutical compositions with the desired pharmacokinetic characteristics is known in the art and can be accomplished by a variety of methods. For example, oral controlled delivery systems include dissolution-controlled release (e.g., encapsulation dissolution control or matrix dissolution control), diffusion-controlled release (reservoir devices or matrix devices), ion exchange resins, osmotic controlled release or gastroretentive systems. Dissolution controlled release can be obtained, e.g., by slowing the dissolution rate of a drug in the gastrointestinal tract, incorporating the drug in an insoluble polymer, and coating drug particles or granules with polymeric materials of varying thickness. Diffusion controlled release can be obtained, e.g., by controlling diffusion through a polymeric membrane or a polymeric matrix. Osmotically controlled release can be obtained, e.g., by controlling solvent influx across a semipermeable membrane, which in turn carries the drug outside through a laser-drilled orifice. The osmotic and hydrostatic pressure differences on either side of the membrane govern fluid transport. Prolonged gastric retention may be achieved by, e.g., altering density of the formulations, bioadhesion to the stomach lining, or increasing floating time in the stomach. For a delayed release formulation an enteric coating can be used to cause delivery in a pH of 4.5 to 6.5. For further detail, see the Handbook of Pharmaceutical Controlled Release Technology, Wise, ed., Marcel Dekker, Inc., New York, N.Y. (2000), incorporated by reference herein in its entirety, e.g. Chapter 22 ("An Overview of Controlled Release Systems").

The concentration of C3d-binding compound in these formulations can vary widely, for example from less than about 0.5%, usually at or at least about 1% to as much as 15 or 80% by weight and are selected primarily based on fluid volumes, manufacturing characteristics, viscosities, etc., in accordance with the particular mode of administration selected. Actual methods for preparing administrable compositions are known or apparent to those skilled in the art and are described in more detail in, for example, Remington's Pharmaceutical Science, 15th ed., Mack Publishing Company, Easton, Pa. (1980).

The C3d-binding compound is present in the composition in a therapeutically effective amount; typically, the composition is in unit dosage form. The amount of C3d-binding compound administered will, of course, be dependent on the age, weight, and general condition of the subject, the severity of the condition being treated, and the judgment of the prescribing-physician. Suitable therapeutic amounts will be known to those skilled in the art and/or are described in the pertinent reference texts and literature. Current non-enterically coated doses are about 1.35 $g/m^2$ body surface area and are administered 4-5 times per day. In one embodiment, the dose is administered either one time per day or multiple times per day for chronic disease states (e.g., Sickle Cell Disease) and can be administered in a bolus or IV for acute conditions (e.g., hyperactive complement system). The C3d-binding compound may be administered one, two or three or four times per day. In certain embodiments, the C3d-binding compound is given less than four times per day. In some embodiments, an effective dosage of C3d-binding compound may be within the range of 0.01 mg to 1000 mg per kg (mg/kg) of body weight per day, or from about 0.1 mg/kg to about 100 mg/kg, or from about 0.5 mg/kg to about 20 mg/kg of body weight per day. Further, the effective dose may be 0.5 mg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, and may increase by 25 mg/kg increments up to 1000 mg/kg, or may range between any two of the foregoing values. In some embodiments, the C3d-binding compound is administered at a total daily dose of from approximately 0.25 $g/m^2$ to 4.0 $g/m^2$ body surface area, e.g., at least about 0.5, 0.6, 0.7, 0.8, 0.9, 1.0, 1.1, 1.2, 1.3, 1.4, 1.5, 1.6, 1.7, 1.8, 1.9 or 2 $g/m^2$, or up to about 0.8, 0.9, 1.0, 1.1, 1.2, 1.3, 1.4, 1.5, 1.6, 1.7, 1.8, 1.9, 2.0, 2.2, 2.5, 2.7, 3.0, or 3.5 $g/m^2$. In some embodiments, the C3d-binding compound may be administered at a total daily dose of about 0.5 to 2.0 $g/m^2$ body surface area, 1-1.5 $g/m^2$ body surface area, or 0.5-1 $g/m^2$ body surface area, or about 0.7-0.8 $g/m^2$ body surface area, or about 1.35 $g/m^2$ body surface area. Salts or esters of the same active ingredient may vary in molecular weight depending on the type and weight of the salt or ester moiety. For administration of the dosage form, e.g., a tablet or capsule or other oral dosage form comprising the enterically coated C3d-binding compound, a total weight in the range of approximately 100 mg to 1000 mg is used. Administration may continue for several hours, days, weeks, months or years depending upon the disease or disorder (e.g., acute event or chronic disease).

Compositions useful for administration may be formulated with uptake or absorption enhancers to increase their efficacy. Such enhancers include, for example, salicylate, glycocholate/linoleate, glycholate, aprotinin, bacitracin, SDS, caprate, iron and the like. See, e.g., Fix (J. Pharm. Sci., 85:1282-1285, 1996) and Oliyai and Stella (Ann. Rev. Pharmacol. Toxicol., 32:521-544, 1993).

The enterically coated compositions comprising the C3d-binding compound can comprise various excipients, as is well known in the pharmaceutical art, provided such excipients do not exhibit a destabilizing effect on any components in the composition. Thus, excipients such as binders, bulking agents, diluents, disintegrants, lubricants, fillers, carriers, and the like can be combined with the C3d-binding compound. For solid compositions, diluents are typically necessary to increase the bulk of a tablet so that a practical size is provided for compression. Suitable diluents include dicalcium phosphate, calcium sulfate, lactose, cellulose, kaolin, mannitol, sodium chloride, dry starch and powdered sugar. Binders are used to impart cohesive qualities to a tablet formulation, and thus ensure that a tablet remains intact after compression. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, hydroxyethyl cellulose, and the like), and Veegum. Lubricants are used to facilitate tablet manufacture; examples of suitable lubricants include, for example, magnesium stearate, calcium stearate, and stearic acid, and are typically present at no more than approximately 1 weight percent relative to tablet weight. Disintegrants are used to facilitate tablet disintegration or "breakup" after administration, and are generally starches, clays, celluloses, algins, gums or crosslinked polymers. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. If desired, flavoring, coloring and/or sweetening agents may be added as well. Other optional components for incorporation into an oral formulation herein include, but are not limited to, preservatives, suspending agents, thickening agents, and the like. Fillers include, for example, insoluble materials such as silicon dioxide, titanium oxide, alumina, talc, kaolin, powdered cellulose, microcrystalline cellulose, and the like, as well as soluble materials such as mannitol, urea, sucrose, lactose, dextrose, sodium chloride, sorbitol, and the like.

A pharmaceutical composition may also comprise a stabilizing agent such as hydroxypropyl methylcellulose or polyvinylpyrrolidone, as disclosed in U.S. Pat. No. 4,301,146. Other stabilizing agents include, but are not limited to, cellulosic polymers such as hydroxypropyl cellulose, hydroxyethyl cellulose, methyl cellulose, ethyl cellulose, cellulose acetate, cellulose acetate phthalate, cellulose acetate trimellitate, hydroxypropyl methylcellulose phthalate, microcrystalline cellulose and carboxymethylcellulose sodium; and vinyl polymers and copolymers such as polyvinyl acetate, polyvinylacetate phthalate, vinylacetate crotonic acid copolymer, and ethylene-vinyl acetate copolymers. The stabilizing agent is present in an amount effective to provide the desired stabilizing effect; generally, this means that the ratio of C3d-binding compound to the stabilizing agent is at least about 1:500 w/w, more commonly about 1:99 w/w.

The tablets can be manufactured by first enterically coating the C3d-binding compound. In one embodiment, a method for forming tablets herein is by direct compression of the powders containing the enterically coated C3d-binding compound, optionally in combination with diluents, binders, lubricants, disintegrants, colorants, stabilizers or the like. In various embodiments, the tablets are manufactured by blending excipients with the C3d-binding compound, compressing the tablet and enteric coating. As an alternative to direct compression, compressed tablets can be prepared using wet-granulation, dry-granulation or roller compaction processes. Tablets may also be molded rather than compressed, starting with a moist material containing a suitable water-soluble lubricant.

In an alternative embodiment, the enterically coated C3d-binding compounds are granulated and the granulation is compressed into a tablet or filled into a capsule. Capsule materials may be either hard or soft, and are typically sealed, such as with gelatin bands or the like. Tablets and capsules for oral use will generally include one or more commonly used excipients as discussed herein. In various embodiments, the capsule is a non-sealing capsule.

For administration of the dosage form, i.e., the tablet or capsule comprising the enterically coated C3d-binding compound, a total weight in the range of approximately 100 mg to 1000 mg is used. The dosage form is orally administered to a patient suffering from a condition for which a C3d-binding compound would typically be indicated, including, but not limited to, complement mediated diseases or disorders.

The C3d-binding compounds of the disclosure can be used in combination with other therapies useful for treating complement mediated diseases and disorders. Combining two or more drugs with differing mechanisms of action can provide greater protection via additive or synergistic effects or provide additional benefit by increasing the therapeutic window for compounds or possibly by reducing side-effects.

The following examples are intended to illustrate but not limit the disclosure. While they are typical of those that might be used, other procedures known to those skilled in the art may alternatively be used.

EXAMPLES

MD simulations. Explicit solvent MD simulations were performed for C3d and C3d-CR2 using NAMD developed by Phillips et al. (*Comput. Chem.* 26:1781 (2005)). Crystallographic structures of C3d (PDB code 1C3D) and C3d-CR2 (PDB code 3OED) were obtained from the protein data bank (PDB). Missing heavy atoms and hydrogens were added, and molecules were parameterized using the CHARMM27 force field in VMD according to Humphrey et al. (*J Mol Graphics* 14:33 (1996)). Structures were placed in TIP3P water cubes, with a minimum distance of 12 Å between any protein atom and the cube boundary, and sodium and chloride counterions were added to achieve 150 mM ionic strength and neutralization of protein charges. Each system was energy minimized using 25000 steps of conjugate gradient minimization, followed by heating and equilibration steps. After minimization, all protein atoms were harmonically constrained. A force constant of 10 kcal/mol/Å$^2$ was used during heating (62 ps) and the first equilibration stage (50 ps), followed by three equilibration stages (50 ps each) using force constants of 5, 2, and 1 kcal/mol/Å$^2$, respectively. In the final equilibration stage (50 ps), only backbone atoms were constrained (at 1 kcal/mol/Å$^2$). Equilibrated systems were simulated for 20 ns with no harmonic constraints. In all simulations, periodic boundary conditions and particle mesh Ewald electrostatics were employed, with nonbonded interaction cutoff and switching distance of 12 and 10 Å, respectively. Bonds involving hydrogen atoms were fixed using SHAKE, and 2 fs integration time steps were used. Langevin temperature and pressure controls were used for all NPT ensemble simulations.

Dynamic pharmacophore models. The MD trajectory of C3d-CR2 was used to develop dynamic pharmacophore models. The trajectory was analyzed using the Bio3D package developed by Grant et al. (S. D. *Bioinformatics* 22:2695 (2006)), in R and UCSF Chimera according to Pettersen et al. (*J. Comput. Chem.* 25:1605 (2004)), and occupancies of nonpolar interactions, hydrogen bonds, and salt bridges were calculated. CR2 residues participating in persistent intermolecular salt bridges, hydrogen bonds, or nonpolar interactions (>50% occupancy) were selected as tentative pharmacophore points. Atoms of the relevant chemical groups in each selected residue were identified, and mean positions of centers of mass were calculated. A freestyle pharmacophore hypothesis was generated using Phase developed by (1) Dixon et al. (*Comput Aided Mol Des* 20:647 (2006)) and (2) Dixon et al. (*Chem Biol Drug Des* 67:370 (2006)), with 24 features corresponding to mean center-of-mass positions of specified CR2 residues. Feature types were defined based on the physicochemical properties of the CR2 atoms used to select them. The conformational flexibility (positional variability) of each feature was calculated from the MD trajectory, and used to define the tolerance radii of each corresponding feature of the pharmacophore model. Additionally, three hydrophobic/aromatic features were manually placed at the bottom of the C3d cavity, in order to "anchor" small molecules deep within the C3d cavity to facilitate energetically favorable binding. From a total of 27 pharmacophore features, subsets of 3-5 features were defined, using inter-feature distances, diversity of feature types, and experimental mutagenesis/binding/functional data as selection criteria. A total of 84 pharmacophore models were selected for screening. The source of screening molecules in this study was the drug-like, in-stock subset developed by Lipinski, C. A. (*J Pharmacol Toxicol Methods* 44:235 (2000)) of the ZINC 12 Database developed by Irwin et al., (*J. Chem. Inf. Model.* (2012)), consisting of at least 7.1 million molecules. All molecules in this database are available for purchase from commercial vendors, and possess drug-like properties. Conformer generation was performed using Phase, resulting in ~160 conformers per molecule on average. Conformers were aligned with each pharmacophore model, with exclusion volumes to prevent overlap with C3d residues.

Docking. All molecules identified in pharmacophore screens were docked to the CR2 binding region on C3d. A total of 400 MD snapshots of C3d (200 from each trajectory) were clustered based on the all-atom RMSD of C3d residues involved in CR2 binding. Representative snapshots from distinct clusters were selected, resulting in five C3d structures (four from the C3d-CR2 simulation and one from the free C3d simulation) with ≥1.75 Å RMSD from each other. Docking was performed using AutoDock Vina developed by Trott et al. (*J. Comput. Chem.* (2009)). The C3d structures and ligands were processed using AutoDockTools, and docked within a grid measuring 40 Å×40 Å×40 Å, with increased exhaustiveness parameter to enhance search accuracy within the enlarged grid. The top 20 docked poses of each molecule were returned after docking.

Scoring. All docked molecule poses were scored using the Vina scoring function. Predicted binding energies were reported for docking to each C3d conformation, and mean energies (across all C3d conformations) were used as a ranking metric. In addition, docked poses were rescreened against all pharmacophore models "in-place", to identify molecules that docked in positions that overlapped with two or more pharmacophore features. Docked poses were also subjected to RMSD-based clustering to identify molecules with low-energy poses that bind in similar conformations to all C3d conformations. A combination of all scoring methods was used for selection of molecules for experimental testing.

Small molecule preparation. Selected drug-like compounds were obtained from Enamine, Pharmeks, ChemDiv, ChemBridge, and Maybridge. Stock solutions were prepared by dissolving molecules in DMSO to concentrations of 4 mM (with no visible precipitation), and stored at −20° C. until used. In all assays, molecules were dissolved further in appropriate aqueous buffer, to minimize effects of DMSO, and DMSO (at an equivalent final concentration) was used in control samples.

Microscale thermophoresis. Direct binding of molecules was assayed using a Monolith NT.115 (NanoTemper Technologies GmbH). Purified C3d (Complement Technology, Inc.) was labeled with NT647 dye using the kit from NanoTemper Technologies, and dissolved to 10 nM in MST buffer (50 mM Tris-HCl, 150 mM NaCl, 10 mM $MgCl_2$, 0.05% Tween 20) containing 5% DMSO. A dilution series of each molecule was prepared in MST buffer containing 5% DMSO, and preincubated with 10 nM NT647-labeled C3d for 10 minutes at room temperature in the dark. Samples were loaded into hydrophilic capillary tubes, and measurements were obtained. For each molecule, reported KD values and binding curves represent results from three independent experiments.

Absorption and fluorescence spectroscopy. Stock solutions of C3d-binding compounds (in DMSO) were diluted in spectroscopic grade acetonitrile (Fisher Scientific). The concentration of each sample was adjusted such that the absorption at the excitation wavelength was below 0.2, after correcting with blank acetonitrile solutions containing the same concentration of DMSO as the measured samples. The UV/visible absorption spectra (260-700 nm) were recorded on a JASCO V-670 spectrophotometer (Tokyo, Japan), using quartz cuvettes (1.0 cm path length, 3.0 ml total volume). The emission spectra were collected with a FluoroLog-3 spectrofluorometer (Horiba-Jobin-Yvon, Edison, N.J., USA). All samples were purged with argon prior to the measurements and all measurements were performed at room temperature.

Fluorescence quantum yield measurements. Fluorescence quantum yield values for the small molecules were calculated using one or more standard quantum yield fluorophores. Values were calculated according to Eq. 1.

$$\Phi_S = \Phi_R \left(\frac{I_S}{I_R}\right) \left(\frac{1-10^{-A_R}}{1-10^{-A_S}}\right) \left(\frac{n_S}{n_R}\right)^2 \qquad \text{EQ. 1}$$

where R and S subscripts denote reference compound and sample, respectively, $\Phi_{fl}$ is quantum yield, $I_n$ is the total integrated fluorescence spectrum intensity obtained from integration of the emission spectra, $A_n$ is sample absorbance at the excitation wavelength, and $n_n$ is the refractive index of the solvent. Reference compounds used for calculation included naphthalene ($\Phi_R$=0.23 for EtOH), anthracene ($\Phi_R$=0.27 for EtOH), and coumarin 1 ($\Phi_R$=0.73 for EtOH). Standard molecule quantum yield measurements were performed in acetonitrile, and solvent-dependent measurements were performed in spectroscopic grade methanol, ethanol, 1-propanol, 1-butanol, ethylene glycol, glycerol, and phosphate buffered saline.

Figure 2:
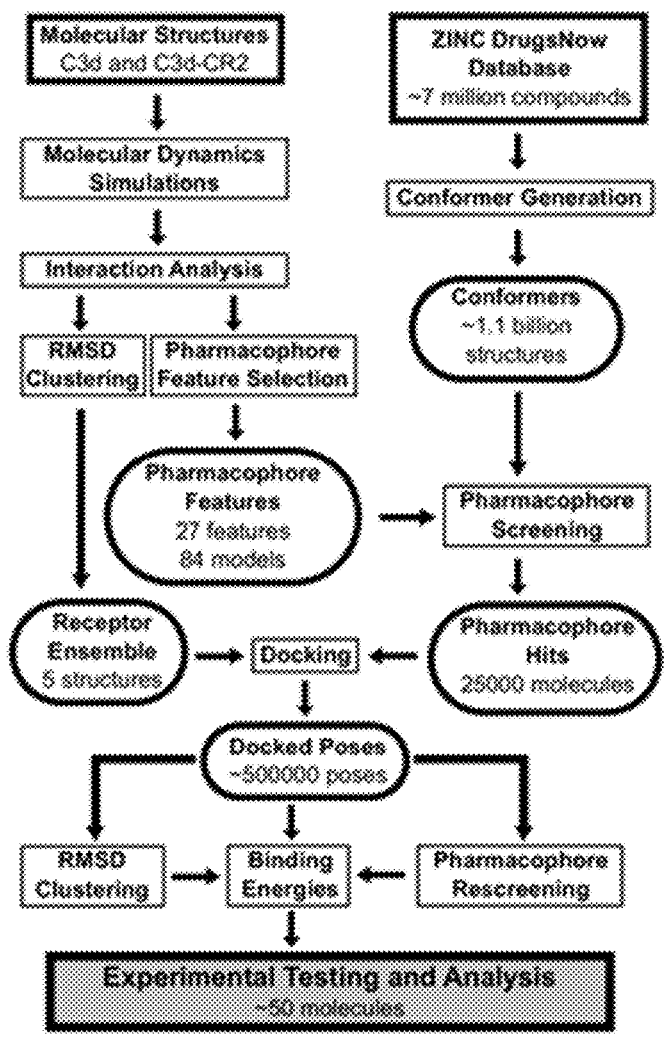
FIG. 2 presents an overview of virtual high-throughput screening framework. Required inputs are shown in the top boxes (white with dark outline), computational methods in white boxes with light outline, and intermediate outputs in white ovals. The framework leads to selection of molecules for experimental testing, shown in the gray box at the bottom.

Virtual high-throughput screening protocol. A multi-step virtual high-throughput screening framework was employed to efficiently screen more than 7 million commercially-available drug-like compounds for predicted C3d binding (see FIG. 2). The screen was guided by known structural, computational, and experimental data regarding C3d and C3d-ligand interactions. First, MD simulations of free C3d and the C3d-CR2 complex were performed. The simulations analyzed interactions and conformational flexibility in each trajectory. Interaction data, in conjunction with available experimental mutagenesis data for C3d and CR2, were used to define pharmacophore features and derive sets of pharmacophore models for the initial compound screen. Conformers of ZINC compounds were generated in order to account for compound flexibility, and screened these conformers against 84 pharmacophore models, yielding ~25000 unique compounds that matched three or more pharmacophore features in at least one model. Each of the pharmacophore hits were docked to five distinct conformations of C3d, derived from RMSD based clustering of binding site residues from MD trajectory snapshots of C3d, both free and in complex with CR2. Lowest energy binding poses for each molecule (and their corresponding binding energies) were reported. Since molecules were free to dock anywhere within the C3d-CR2 binding cavity, many binding poses varied considerably from one another. RMSD clustering of poses were used to identify compounds that docked in a similar conformation to all receptor conformations. Furthermore, docked poses were rescreened against pharmacophore models, to identify compounds that exhibited low energy binding and desired physicochemical property distribution simultaneously.

C3d-ligand interaction analysis. C3d is a molecular hub for both host and pathogenic proteins. Interestingly, the majority of known C3d ligands bind at a concave acidic face of the molecule, opposite the reactive thioester responsible for cell surface attachment (see FIG. 3A). Structural, biochemical, and biophysical data were leveraged on these interactions to guide the search for C3d-binding small molecules. Interestingly, all of the crystallographic structures of C3d (free and complexed) have a deep cavity preserved in the center of the acidic face. Since the rest of C3d has a relatively flat or convex surface, this cavity represents an attractive target for small molecule binding. While many ligands bind C3d at the acidic face, CR2 binds entirely over the cavity on its surface (see FIGS. 3B and 3C). Thus, the small molecule screen was focused on the C3d-CR2 interaction.

MD simulations of the C3d-CR2 complex were performed, in order to evaluate the conformational flexibility of the C3d-CR2 binding site, and to elucidate which residues are crucial to the C3d-CR2 interaction. Similar to most known ligands of C3d, CR2 binds at the concave acidic region of C3d (see FIGS. 3B and 3C), and binding is dominated by electrostatic interactions. Through initial examination, a deep cavity is observed in the concave acidic region of C3d, and this cavity persists during MD simulations of both free C3d and the C3d-CR2 complex. Interestingly, CR2 itself does not "enter" the cavity, but rather resides atop the cavity, forming polar and nonpolar interactions with a ring of C3d residues lining the perimeter of the cavity (see FIG. 3B). The C3d interaction ring can be divided into four sectors, based on physicochemical interaction type and spatial distribution. Sectors 1 (red) and 3 (green) consist primarily of electrostatic interactions, while sectors 2 (orange) and 4 (purple) are involved in hydrogen bonding and nonpolar interactions. Residues in sectors 1-3 are also crucial for interactions between C3d and staphylococcal virulence factors Efb-C, Ecb, and Sbi-IV, all of which have been shown (both structurally and functionally) to competitively inhibit C3d-CR2 interaction (see FIG. 3A). Thus, since these C3d residues are critical for binding of multiple natural ligands, they represent important targets for identification and design of potential diagnostic and therapeutic molecules.

Figure 3:
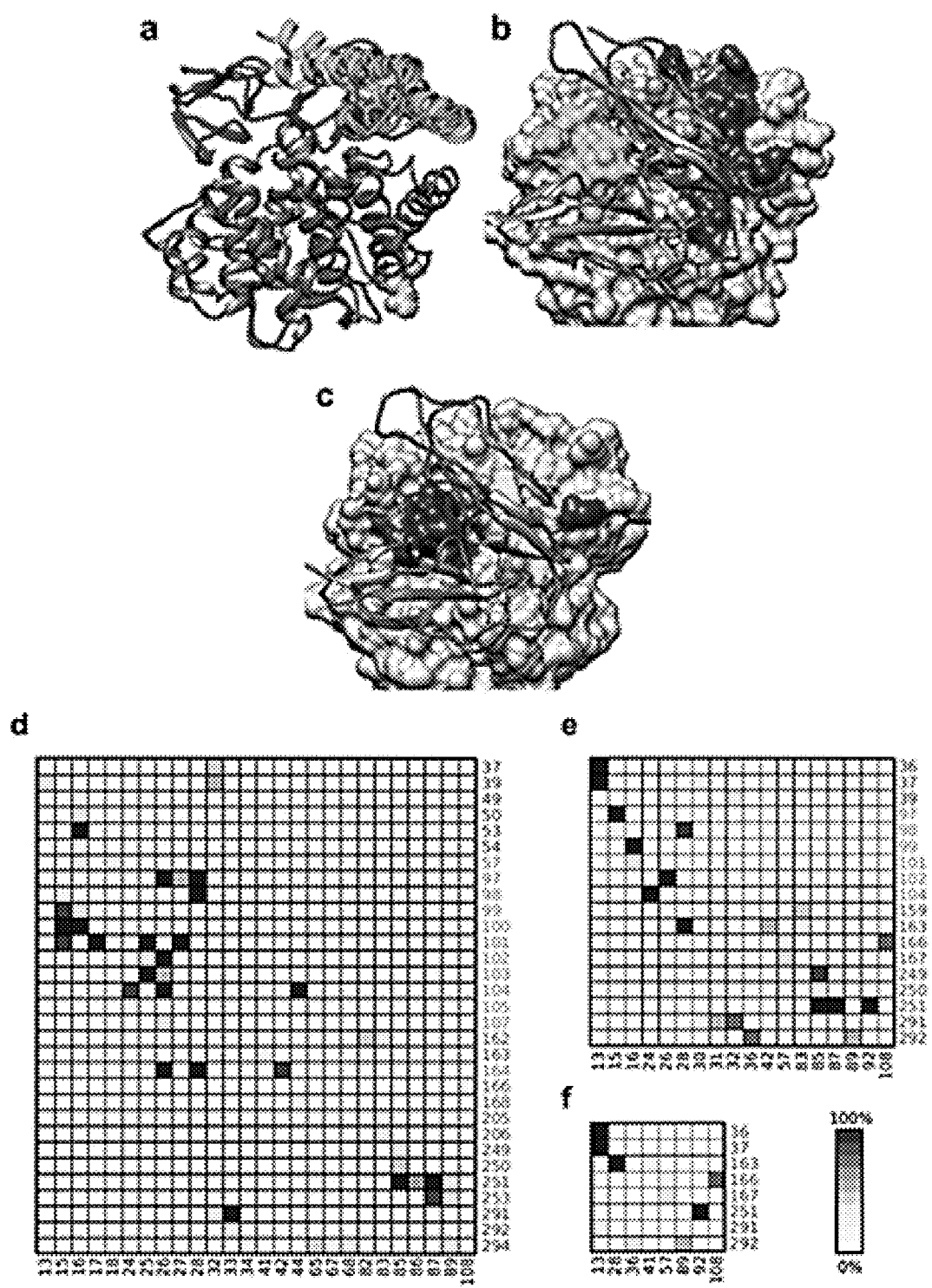
FIG. 3A-F Analysis of C3d-ligand interactions. (A) The molecular graphic shows superimposed co-crystal structures of C3d (gray) in complex with Efb-C (green), Ecb/Ehp (orange), Sbi-IV (cyan), and CR2 (magenta). The location of the thioester (for cell surface attachment) is shown in gold. (B) Examination of intermolecular interactions from the C3d-CR2 crystallographic structure reveals a ring of interactions surrounding a deep cavity on the C3d surface. The figure shows interacting regions of C3d, divided into four sectors; acidic cluster 1 (red), nonpolar cluster (orange), acidic cluster 2 (green), and polar cluster (purple). (C) The C3d surface and CR2 side chains are colored by their effect on experimental binding affinity compared to the wild-type C3d-CR2 complex; <25% binding (red), 25-59% binding (orange), 60-84% binding (yellow), and >125% binding (black). C3d-CR2 interaction occupancies were calculated throughout a 20 ns MD trajectory, and nonpolar interactions (D), hydrogen bonds (E), and salt bridges (F) are shown here. CR2 residues are on the x-axes, and C3d residues on the y-axes. C3d residue labels are colored according to their corresponding sector (from Panel b).

The interaction between C3d and CR2 has been well studied in the last decade. A large amount of mutagenesis data is available. Mutations of C3d and CR2, and their relative effects on binding, are shown in FIG. 3C. Naturally, the locations of inhibitory mutations (red, orange, and yellow) correspond to the ring of interactions seen in FIG. 3B. Whereas inhibitory mutations are spatially disbursed, it was noticed that the highest inhibitory mutations are observed in sectors 1 and 3, and involve primarily mutations of charged residues. Therefore, while all persistent interactions from MD simulations were considered during vHTS of C3d (see FIG. 3D-F), charge-charge interactions (see FIG. 3F) were given special consideration in development of pharmacophore models and postprocessing/re-ranking of lead compounds after docking.

Figure 4:
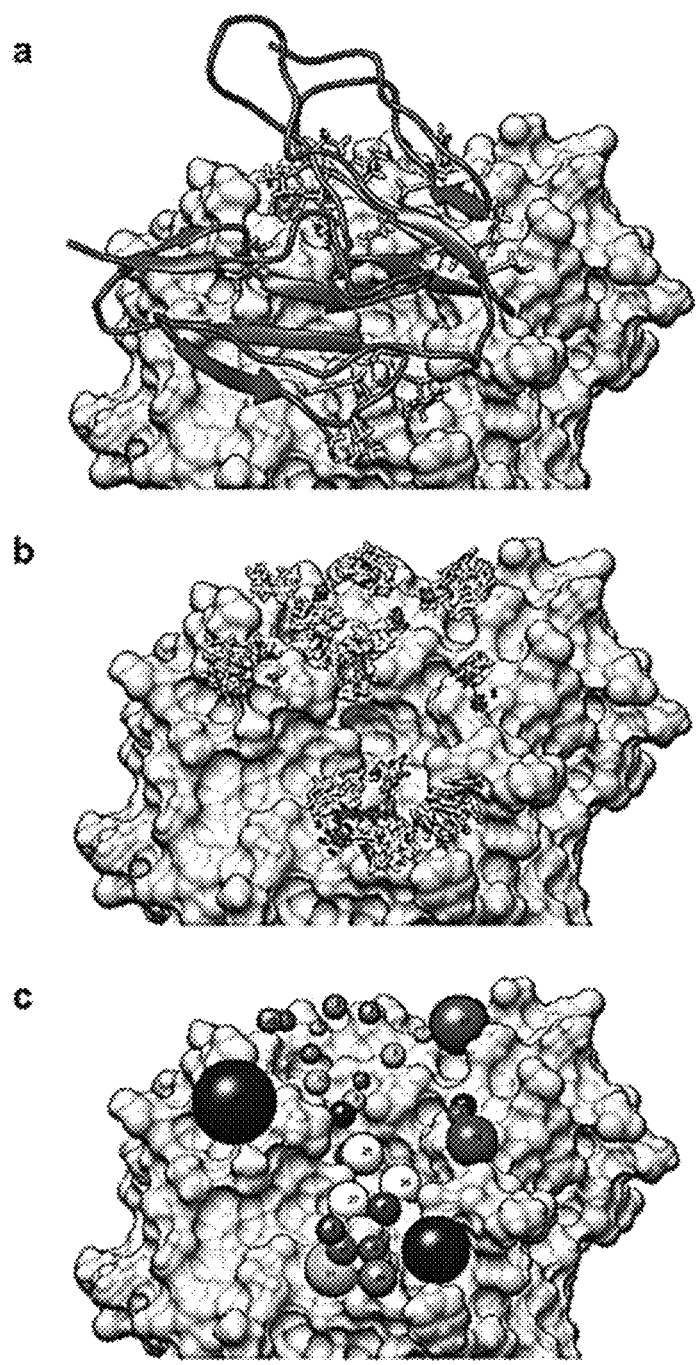
FIG. 4A-C presents the development of a dynamic pharmacophore model based on C3d-CR2 interaction. (A) C3d (tan surface) is shown in complex with CR2 (ribbon), with interacting side chains of CR2 shown as sticks colored by element type (carbon, gray; nitrogen, blue; oxygen, red; hydrogen, white). (B) Positions of chemical groups from CR2 residues interacting with C3d are shown, at 10 different time points during the 20 ns MD trajectory. The physicochemical properties and spatial distribution of the atom groups were used to define the 27 pharmacophore features observed in (C). Features are colored by pharmacophore type (hydrogen bond donor, green; hydrogen bond acceptor, magenta; positive charge, blue; negative charge, red; aromatic, brown; and hydrophobic, gray).

Pharmacophore screening. The next step in the vHTS protocol involved searching for molecules with similar geometric and spatial arrangement of physicochemical properties to CR2. Based on the MD simulation of C3d-CR2 and previous experimental mutagenesis data, several CR2 residues found important for its interaction with C3d were selected (see FIG. 4A). The arrangement of selected functional moieties (isolated from CR2 residues) is shown in FIG. 4B, with respect to C3d. These moieties were used to define 24 pharmacophore features of varying types (e.g., positive, negative, hydrogen bond acceptor or donor, aromatic, hydrophobic), based on the physicochemical properties of each moiety itself (see Table 1 and FIG. 4C). Since these atoms fluctuated to varying degrees over time, tolerance spheres were generated with radii large enough to incorporate 95% of their occupied positions. In addition, three aromatic features were defined in the bottom of the C3d cavity, in order to "anchor" small molecules into the cavity.

TABLE 1

List of the 27 pharmacophore features used.

| Feature | Type[1] | Residue[2] | Residue Atoms[3] | C3d Residue Partners | Tolerance (Å)[4] |
|---|---|---|---|---|---|
| 1 | P(D) | R13 | Cζ, Nη1, Nη2 | D36, E37 | 1.94 |
| 2 | P(D) | R28 | Cζ, Nη1, Nη2 | D163 | 1.57 |
| 3 | P(D) | R89 | Cζ, Nη1, Nη2 | D292 | 3.93 |
| 4 | P(D) | K108 | Nζ | E166 | 2.71 |
| 5 | N(A) | D92 | Cγ, Oδ1, Oδ2 | K251 | 2.02 |
| 6 | D | S15 | Oγ | V97, N98 | 0.59 |
| 7 | D | Y16 | N | L99, A101 | 0.74 |
| 8 | D | V26 | N | I102 | 0.71 |
| 9 | D | R28 | Nε | N98 | 0.91 |
| 10 | D | S42 | Oγ | D163 | 1.05 |
| 11 | D | S85 | Oγ | Q249, L250, K251 | 1.42 |
| 12 | A | G24 | O | S104 | 1.43 |
| 13 | A | C31 | O | K291 | 1.29 |
| 14 | A | S32 | O | E39, K291 | 2.36 |
| 15 | A | S85 | O | Q249, L250, K251 | 1.15 |
| 16 | A | P87 | O | K251 | 1.00 |
| 17 | R | Y16 | Cγ, Cδ1, Cε1, Cζ, Cδ2, Cε2 | R49, Q50, L53, E54, K57, L99, I100 | 4.03 |
| 18 | R | Y88 | Cγ, Cδ1, Cε1, Cζ, Cδ2, Cε2 | — | 4.03 |
| 19 | H | T25 | Cγ2 | A101, I102, D103 | 1.78 |
| 20 | H | V26 | Cγ1, Cγ2 | V97, I102, D103, S104, L107, I164 | 1.78 |
| 21 | H | I27 | Cβ, Cγ2, Cγ1, Cδ | V97, A101 | 1.80 |
| 22 | H | R28 | Cβ, Cγ, Cδ | V97, N98, I164 | 2.68 |
| 23 | H | L44 | Cδ1, Cδ2 | S104, Q168 | 1.59 |
| 24 | H | P87 | N, Cδ, Cα, Cβ, Cγ | K251, F253 | 2.62 |
| 25 | R | — | — | S94, L95, N98, E160 | 2.00 |

TABLE 1-continued

List of the 27 pharmacophore features used.

| Feature | Type[1] | Residue[2] | Residue Atoms[3] | C3d Residue Partners | Tolerance (Å)[4] |
|---|---|---|---|---|---|
| 26 | R | — | — | H33, Q284, Q288 | 2.00 |
| 27 | R | — | — | K91, E160, Y201, Q205 | 2.00 |

[1]Feature Types: D (hydrogen-bond donor), A (hydrogen-bond acceptor), P (positive), N (negative), H (hydrophobic), R (aromatic).
[2]Residue types and numbers correspond to CR2 residues and numbering (from PDB code 3OED).
[3]Atoms from residues used to derive features (also used associated hydrogen atoms - not listed).
[4]Tolerance reflects size of pharmacophore feature used for molecule screening.

Pharmacophore models were selected from subsets of the 27 features, in order to optimize the number of hits, specificity, and screen time. The first parameter in model selection was the number of pharmacophore features. Using too few features often yields large numbers of false positives in pharmacophore screens, whereas using too many features may be too stringent during the search, yielding few or no hits at all. By selecting pharmacophore models that contain between three and five features, a balance between specificity and diversity in molecule hits can be achieved. Since the interfeature distances in the initial model are quite variable, a distance criteria was also applied in model selection. Selected models had interfeature distances of at least 4 Å and less than 15 Å. These criteria alleviate fortuitous matching of multiple features by a single chemical moiety, while constraining the search to distances that can reasonably be spanned by a drug-like small molecule (MW<500). Finally, the model selection was restricted based on properties of specific features. Models were selected to contain one hydrophobic feature from the cavity base (Features 25, 26, or 27), one positive feature (Features 1-4), one feature representing a crucial interaction based on experimental binding data (Features 1, 2, 5, 6, 9-11, 13-16, 18, 20, 22, or 24), and no more than one additional hydrophobic feature (see Table 1). These criteria result in physicochemically diverse pharmacophore models that explore multiple regions of the C3d-CR2 interaction site.

In total, 84 pharmacophore models were selected, and conformers for generated ZINC compounds were screened against each model. It was found that three-feature models were highly nonspecific and yielded very large numbers of hits. Models containing features from sector 4 also yielded large numbers of hits. Since sector 4 is less important than other sectors for C3d-ligand interactions, models comprised of features from sectors 1-3 were preferred, with either four or five features. The search was narrowed to 51 models (27 of which yielded at least 1 hit), resulting in a total of 25668 unique compounds.

Figure 5:
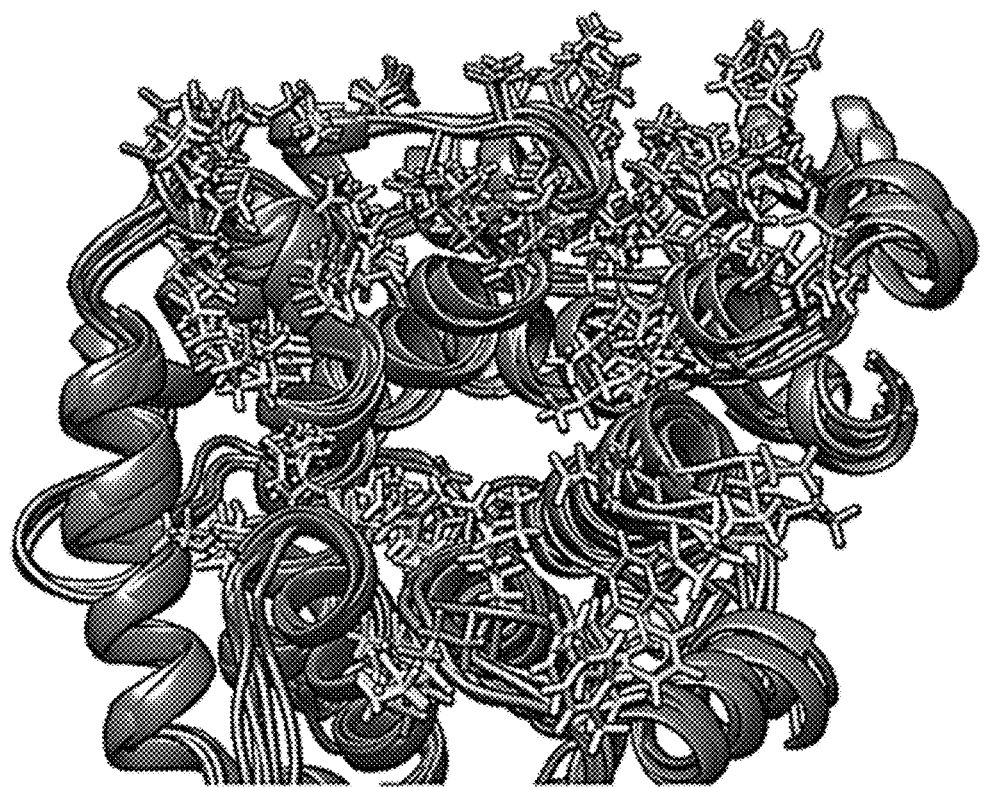
FIG. 5 presents a C3d conformational ensemble from 20 ns MD simulation and RMSD-based clustering. Residue side chains used for RMSD clustering criteria are shown as sticks, and the different colors correspond to conformations of the side chains in five different receptor structures.
Figure 6A:
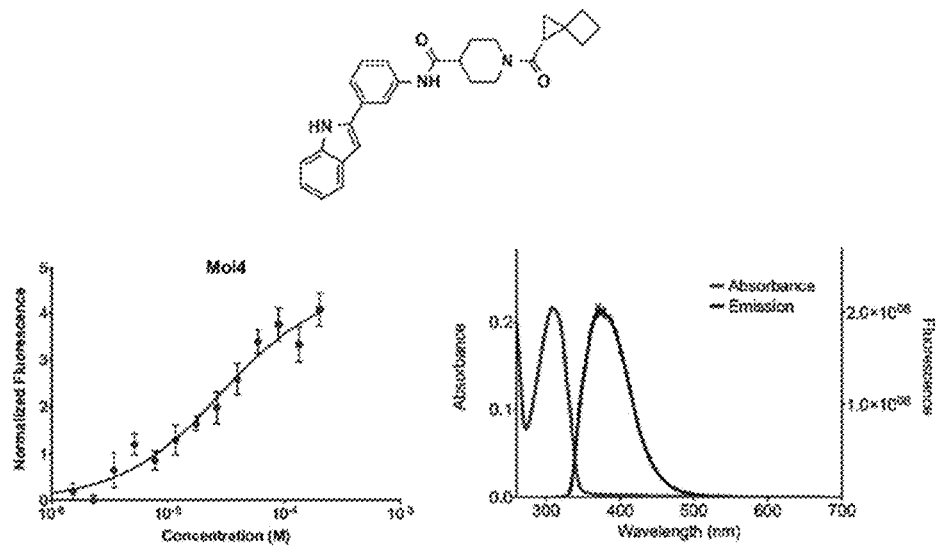
FIG. 6A-D provides chemical structures, binding, and fluorescence data for four top-performing molecules from virtual high-throughput screen. Data is shown for Mol4 (A), Mol 16 (B), Mol17 (C), and Mol42 (D). Chemical structures are shown in the left panels, concentration-dependent thermophoresis binding curves in the center panels, and absorption and emission spectra in the right panels.
Figure 6B:
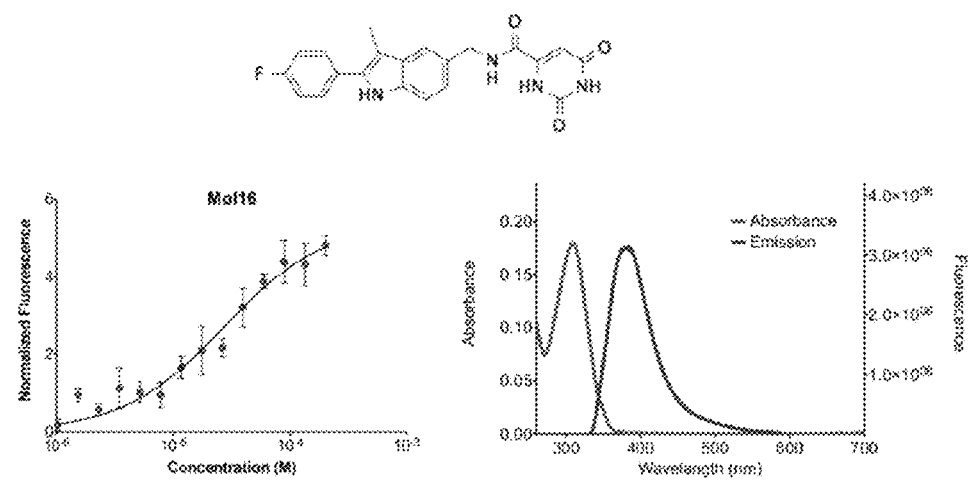
Figure 6C:
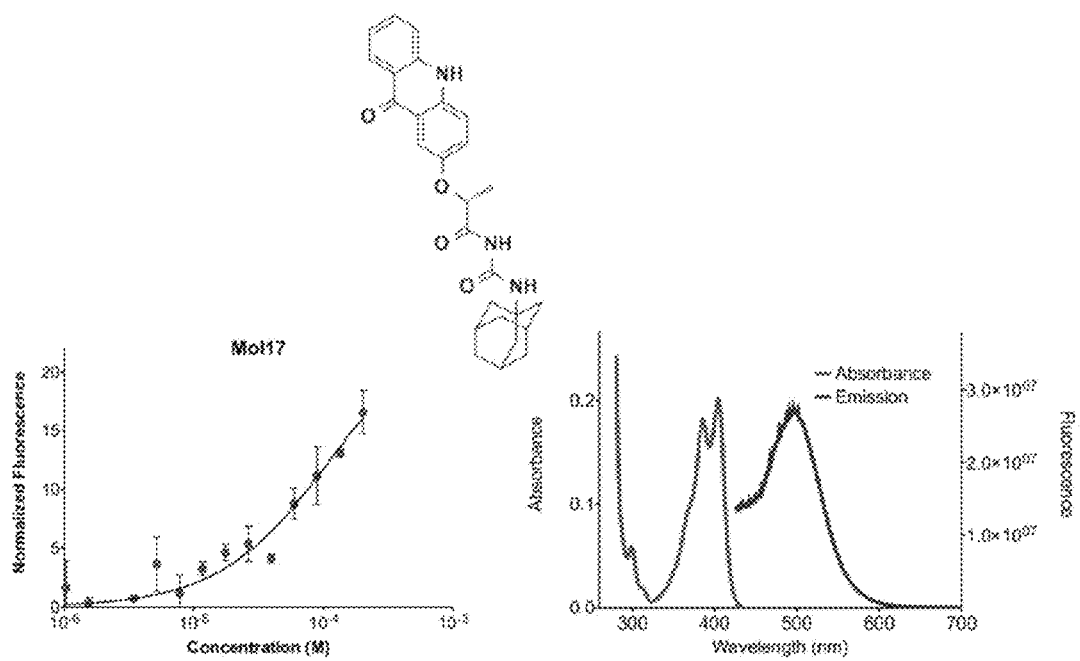
Figure 6D:
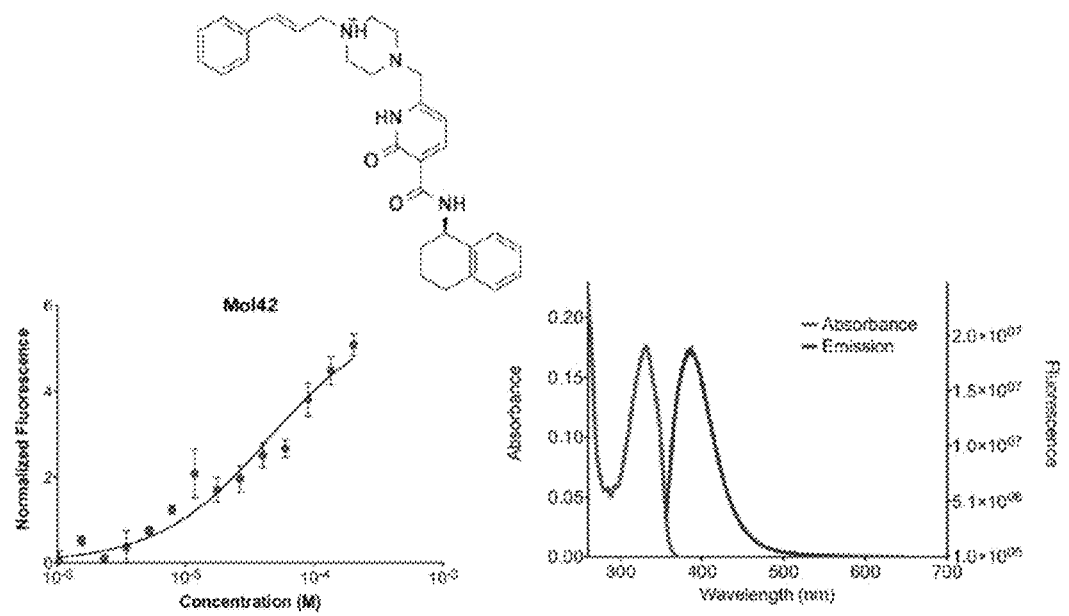

Docking and Postprocessing. Incorporation of target protein flexibility improves the accuracy of docking simulations. However, accounting for ligand-induced conformational change in the target binding site is not feasible for large numbers of molecules using current computational resources. As an alternative, one can dock small molecules to a structurally-diverse ensemble of target protein conformations, in order to increase the probability of encountering a binding site conformation resembling the conformation of the ligand-bound state. A protocol similar to the relaxed complex scheme (RCS) described in Lin et al. (*Biopolymers* 68:47 (2003)) and Amaro et al. (*J Comput Aided Mol Des* 22:693 (2008)) was followed, in which molecules were docked to a conformational ensemble of C3d to implicitly incorporate receptor flexibility into docking simulations. From MD simulations of free C3d and the C3d-CR2 complex, C3d structures were clustered based on RMSD of interacting residues, as determined from the C3d-CR2 MD simulation (see FIGS. 3D and 3F). This method allowed for selection of C3d structures with the most diverse CR2 binding modes. Five structures were obtained, with RMSD for binding site residues between 2 and 3 Å for all structure pairs. The low pairwise RMSD values indicate robust structure within the binding site. FIG. 5 shows the superposition of the five selected C3d structures from RMSD clustering, which shows similar positions for side chains of CR2-interacting residues, regardless of whether C3d is free or complexed.

Since a large protein-protein interface was explored as the molecular target, it was of interest to examine where compounds dock within the entire binding site. Thus, during docking simulations, compounds were allowed to dock within a large (40×40×40 Å) grid surrounding the acidic concave region of C3d (see FIG. 5). Molecules were docked to the five C3d conformations mentioned above, and predicted binding energies were reported for low-energy docked poses, based on the AutoDock Vina scoring function.

While many docked poses had low predicted binding energies (as low as −10.1 kcal/mol), some compounds bound strongly to a small number of C3d conformations, and poorly to others. Some molecules docked in very different orientations to different C3d conformations, and others docked deep in the C3d cavity, such that inhibition of CR2 binding would be improbable. Low energy compounds were clustered, based on RMSD of their docked conformations to the five diverse C3d structures, and compounds that had similar molecule binding modes (<5 Å RMSD) to all five structures were identified. Additionally, all docked poses were rescreened against the pharmacophore models used in the initial screening round, by checking whether molecule docked poses had chemical groups that overlapped with pharmacophore features. Compounds were selected that matched at least two pharmacophore features, while docked to at least three different C3d structures. A list of hits with <−6.8 kcal/mol mean binding energy (corresponding to KD=10 μM at room temperature) were selected that met the RMSD and pharmacophore postprocessing criteria, yielding 14 compounds. In addition, additional compounds were selected that met RMSD criteria with energies <−8.0 kcal/mol, as top-binding compounds. A total of 49 compounds were selected for experimental evaluation (see Table 2).

TABLE 2

The 49 chemical compounds selected for experimental evaluation.

| No | ZINC ID | R1 | R2 | R3 | K4 | R5 | Mean | Charge | MW | RMSD Rank | Rank |
|---|---|---|---|---|---|---|---|---|---|---|---|
| B1 | ZINC02520169 | −9.7 | −8.2 | −8.9 | −8.8 | −9.1 | −8.94 | 0 | 500.0 | 3 | 1 |
| B2 | ZINC15962406 | −9.6 | −8.4 | −8.1 | −8.3 | −9.4 | −8.76 | 0 | 448.5 | 16 | 4 |
| B3 | ZINC09980865 | −9.1 | −8.2 | −9.0 | −8.3 | −8.8 | −8.72 | 0 | 491.6 | 1 | 7 |

TABLE 2-continued

The 49 chemical compounds selected for experimental evaluation.

| No | ZINC ID | R1 | R2 | R3 | K4 | R5 | Mean | Charge | MW | RMSD Rank | Rank |
|---|---|---|---|---|---|---|---|---|---|---|---|
| B4 | ZINC11933334 | −9.6 | −8.2 | −8.6 | −8.4 | −8.8 | −8.72 | 0 | 427.5 | 28 | 8 |
| B5 | ZINC14749391 | −9.1 | −8.4 | −8.4 | −8.5 | −9.0 | −8.68 | 1 | 499.7 | 7 | 11 |
| B6 | ZINC08826044 | −9.0 | −8.0 | −8.7 | −8.1 | −9.5 | −8.66 | 1 | 493.6 | 4 | 13 |
| B7 | ZINC09963258 | −8.4 | −8.3 | −8.7 | −9.1 | −8.8 | −8.66 | 0 | 485.5 | 6 | 14 |
| B8 | ZINC15825209 | −8.7 | −8.0 | −8.8 | −7.9 | −9.9 | −8.66 | 0 | 457.5 | 15 | 15 |
| B9 | ZINC09573345 | −8.8 | −8.2 | −8.3 | −7.8 | −9.8 | −8.62 | 0 | 441.5 | 35 | 19 |
| B10 | ZINC05093827 | −8.8 | −8.2 | −8.1 | −8.2 | −9.5 | −8.56 | 1 | 382.4 | 13 | 26 |
| B11 | ZINC09714883 | −8.6 | −7.7 | −8.8 | −8.5 | −9.0 | −8.52 | 0 | 460.4 | 22 | 33 |
| B12 | ZINC09609305 | −9.1 | −8.3 | −8.1 | −8.0 | −9.0 | −8.50 | 0 | 487.6 | 21 | 41 |
| B13 | ZINC17146977 | −8.9 | −7.9 | −8.1 | −7.9 | −9.6 | −8.48 | 1 | 461.3 | 40 | 46 |
| B14 | ZINC09336876 | −9.1 | −8.0 | −8.0 | −8.4 | −8.8 | −8.46 | 0 | 489.3 | 5 | 55 |
| B15 | ZINC24760364 | −8.6 | −7.9 | −8.0 | −8.3 | −9.5 | −8.46 | 0 | 463.5 | 12 | 60 |
| B16 | ZINC71749000 | −8.9 | −8.0 | −8.1 | −8.1 | −9.2 | −8.46 | 0 | 392.4 | 49 | 63 |
| B17 | ZINC12522154 | −8.7 | −8.0 | −8.4 | −8.4 | −8.7 | −8.44 | 0 | 459.5 | 48 | 68 |
| B18 | ZINC08826002 | −8.4 | −7.7 | −8.4 | −8.8 | −8.7 | −8.40 | 0 | 479.8 | 55 | 81 |
| B19 | ZINC32951574 | −8.8 | −8.1 | −7.8 | −8.5 | −8.8 | −8.40 | 0 | 445.5 | 31 | 83 |
| B20 | ZINC33037466 | −9.0 | −7.6 | −7.9 | −8.6 | −8.9 | −8.40 | 0 | 426.5 | 60 | 84 |
| B21 | ZINC09117544 | −8.7 | −8.0 | −8.0 | −8.2 | −9.0 | −8.38 | 1 | 446.6 | 26 | 88 |
| B22 | ZINC12912690 | −8.8 | −7.9 | −8.5 | −8.5 | −8.1 | −8.36 | 0 | 458.5 | 9 | 97 |
| B23 | ZINC14541866 | −8.9 | −8.0 | −8.0 | −7.9 | −8.9 | −8.34 | 1 | 445.6 | 30 | 110 |
| B24 | ZINC33116506 | −8.5 | −7.5 | −8.7 | −8.2 | −8.8 | −8.34 | 0 | 459.3 | 19 | 112 |
| B25 | ZINC06181558 | −8.2 | −7.9 | −7.7 | −8.5 | −9.3 | −8.32 | 0 | 454.9 | 46 | 121 |
| B26 | ZINC11964524 | −8.6 | −7.9 | −8.6 | −8.2 | −8.3 | −8.32 | 1 | 443.6 | 18 | 128 |
| B27 | ZINC09468232 | −8.4 | −8.1 | −8.3 | −7.9 | 8.8 | −8.30 | 0 | 479.5 | 10 | 143 |
| B28 | ZINC12548325 | −8.4 | −7.5 | −8.4 | −9.0 | −8.2 | −8.30 | 0 | 492.6 | 20 | 145 |
| B29 | ZINC02922837 | −8.2 | −7.6 | −7.9 | −8.0 | −9.5 | −8.24 | 0 | 426.5 | 45 | 195 |
| B30 | ZINC14992854 | −8.9 | −7.4 | −8.1 | −8.6 | −8.2 | −8.24 | 1 | 475.5 | 58 | 205 |
| B31 | ZINC58139425 | −8.8 | −8.0 | −8.1 | −7.9 | −8.4 | −8.24 | 0 | 445.5 | 61 | 210 |
| B32 | ZINC12486362 | −8.5 | −7.9 | −8.3 | −7.7 | −8.7 | −8.22 | 0 | 454.5 | 39 | 225 |
| B33 | ZINC12677534 | −7.9 | −7.8 | −8.7 | −8.5 | −8.2 | −8.22 | 0 | 486.6 | 64 | 226 |
| B34 | ZINC03642712 | −8.8 | −8.3 | −7.4 | −7.9 | −8.6 | −8.20 | 0 | 404.4 | 38 | 246 |
| B35 | ZINC33284369 | −8.7 | −7.6 | −7.7 | −8.6 | −8.4 | −8.20 | 0 | 449.5 | 67 | 257 |
| B36 | ZINC14980290 | −8.5 | −7.7 | −8.1 | −7.9 | −8.7 | −8.18 | 1 | 469.6 | 56 | 273 |
| B37 | ZINC72301224 | −8.9 | −7.9 | −7.9 | −8.4 | −7.8 | −8.18 | 0 | 494.6 | 37 | 292 |
| B38 | ZINC09604337 | −8.4 | −7.6 | −8.1 | −8.0 | −8.7 | −8.16 | 0 | 482.5 | 27 | 303 |
| B39 | ZINC33284430 | −8.5 | −7.7 | −7.7 | −8.9 | −8.0 | −8.16 | 0 | 469.9 | 68 | 318 |
| B40 | ZINC57270793 | −8.3 | −7.7 | −8.6 | −7.8 | −8.4 | −8.16 | 0 | 472.6 | 42 | 321 |
| B41 | ZINC12541787 | −8.8 | −7.7 | −8.3 | −7.6 | −8.3 | −8.14 | 0 | 466.5 | 29 | 339 |
| B42 | ZINC23360299 | −8.0 | −7.7 | −8.0 | −7.9 | −8.6 | −8.04 | 1 | 483.6 | 66 | 553 |
| B43 | ZINC20915400 | −8.1 | −7.4 | −8.3 | −7.6 | −8.5 | −7.98 | 0 | 442.6 | 584 | 734 |
| B44 | ZINC13362011 | −8.3 | −7.5 | −7.3 | −7.7 | −8.0 | −7.76 | 0 | 407.5 | 2435 | 1863 |
| B45 | ZINC02628238 | −7.5 | −7.2 | −7.6 | −8.0 | −7.5 | −7.56 | 0 | 410.9 | 1938 | 3793 |
| B46 | ZINC12151492 | −8.1 | −7.0 | −7.1 | −7.2 | −7.8 | −7.44 | 1 | 439.0 | 3167 | 5458 |
| B47 | ZINC06754062 | −7.0 | −7.7 | −7.5 | −7.2 | −7.7 | −7.42 | 0 | 392.5 | 4310 | 5723 |
| B48 | ZINC09588499 | −8.1 | −7.4 | −7.1 | −7.1 | −7.3 | −7.40 | 0 | 420.5 | 4140 | 6061 |
| B49 | ZINC55080042 | −7.7 | −7.4 | −7.1 | −6.9 | −7.6 | −7.34 | 1 | 407.5 | 2791 | 7239 |

The table shows ZINC IDs of selected molecules vHTS (Round 1), predicted binding energies to C3d structures R1-R5, the mean energy across all structures, charge, molecular weight (MW), and rankings. RMSD rank is the rank of the top binding pose consistent across all receptor structures. Molecules that matched features in pharmacophore rescreen are shown.

Experimental evaluation of C3d binding. In order to validate the hits from vHTS, binding of 49 selected compounds were measured using microscale thermophoresis. All molecules were tested in a concentration-dependent manner; starting at a concentration of 200 μM (most molecules were poorly soluble in aqueous solution above this concentration). Ten molecules were identified that bound to C3d, with binding affinities (KD) ranging between 25-500 μM. The molecular structures and binding curves for top molecules are shown in FIG. 6, and other binding compounds are shown in FIG. 9.

Absorption and fluorescence properties. The ultimate goal is to design small molecules that can be used for optical detection of C3d on tissues in vivo: e.g., a small molecule that can serve as a contrast agent for fluorescence imaging of regions in tissues with overexpression of C3d. Thus, it is critical to evaluate the photophysical properties of C3d-binding compounds and to determine their diagnostic potential. We examined the absorption and fluorescence properties of ten C3d-binding compounds, in order to determine if optical detection is feasible. Because all compounds contain small aromatic moieties and functional groups that mediate extended conjugation, they exhibit pronounced absorption in the UV region and/or the blue edge of the visible spectrum (see FIG. 6 and FIG. 9). Eight of the ten examined C3d-binding compounds exhibit fluorescence with emission quantum yields ranging from about 0.001 to nearly 1 (Table 3).

TABLE 3

Binding and fluorescence properties of the ten C3d-binding compounds.

| Mol | KD (μM) | Excitation Peak (nm) | Emission Peak (nm) | Quantum Yield |
|---|---|---|---|---|
| 1 | 209 ± 36 | 280/335 | 400/430 | 0.001 |
| 4 | 29 ± 8 | 315 | 380 | 0.560 |

TABLE 3-continued

Binding and fluorescence properties of the ten C3d-binding compounds.

| Mol | KD (µM) | Excitation Peak (nm) | Emission Peak (nm) | Quantum Yield |
|---|---|---|---|---|
| 5 | 68 ± 14 | 280 | 400 | 0.260 |
| 11 | 45 ± 13 | 310 | 405 | 0.001 |
| 16 | 27 ± 5 | 310 | 385 | 0.002 |
| 17 | 116 ± 41 | 390/405 | 500 | 0.984 |
| 22 | 183 ± 81 | 355 | 455 | 0.044 |
| 35 | 417 ± 171 | 275 | 460 | 0.001 |
| 36 | 132 ± 28 | 320 | 425 | 0.017 |
| 42 | 45 ± 15 | 335 | 390 | 0.011 |

As expected, the fluorescence spectra of the compounds containing quinolone moieties, such as Mol22 and Mol36, span between about 400 and 550 nm (see FIG. 9). Similarly, the indole-containing compounds, such as Mol4, Mol5, and Mol16, fluoresce between about 300 and 450 nm (FIG. 6 and FIG. 9). The acridone derivative, Mol17, stands out with intense visible fluorescence and $\Phi_{fl}$ close to unity (see Table 3, and FIG. 6).

To be useful for a fluorescence imaging contrast agent, a compound should exhibit emission enhancement upon binding to the targeted sites on cells and tissues. Similarly, for diagnosis, it is desirable for a molecule to exhibit low quantum yield in its free (unbound) state, and undergo a significant increase in quantum yield upon target binding. That is, the increased effective viscosity or decreased polarity (or change in other conditions) of the microenvironment of the binding site should cause an increase in the emission quantum yield of a compound. As a result, the fluorescence signal is expected to come predominantly from the bound molecules and not from the ones free in solution.

Many of the C3d binding compounds have structures characteristic of "molecular rotors," i.e., they contain single bonds connecting conjugated systems. Torsional modes around these single bonds (that in fact have partial conjugation) provide pathways for non-radiative decay of the excited state, competing with the fluorescence decay. Similar to restraining molecular motions in a binding site, an increased viscosity of the media suppresses such non-radiative pathways leading to an $\Phi_{fl}$ increase.

Figure 7A:
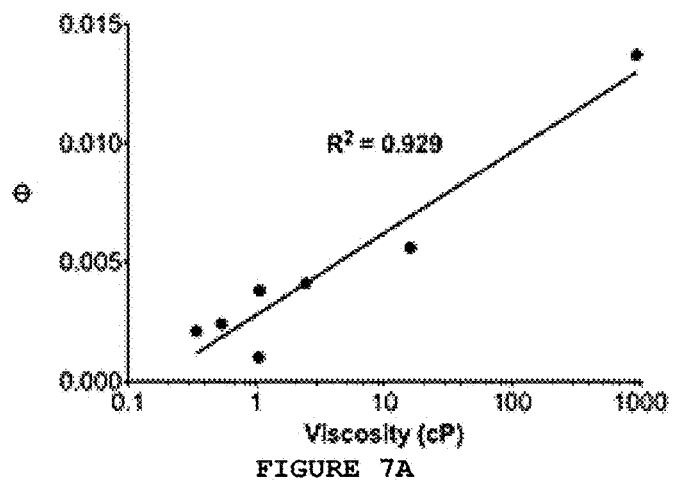
Figure 7B:
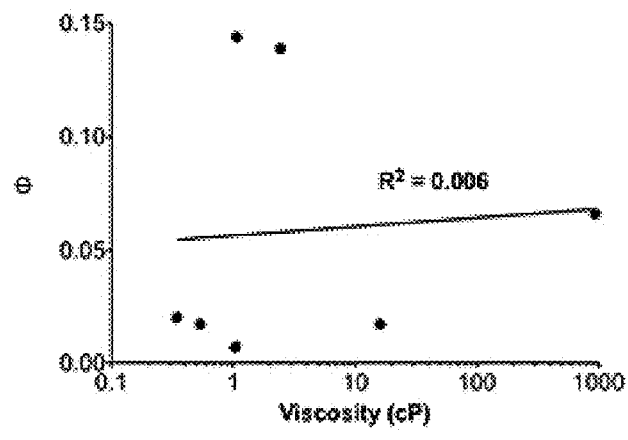
Figure 7C:
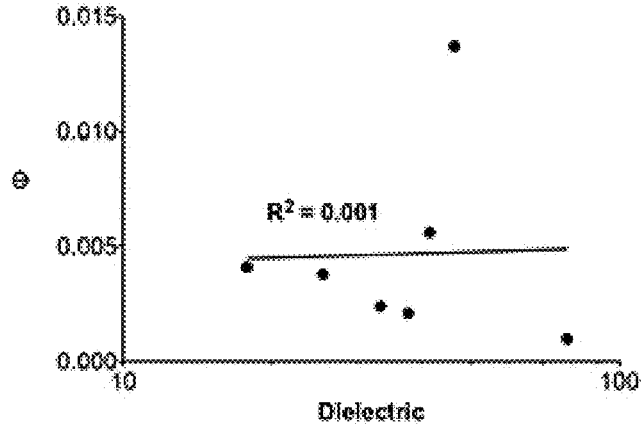

To test the fluorescence dependence on the media viscosity, a protic media was used, i.e., an aqueous buffer and six alcohols with widely varying viscosities. Two of the C3d-binding compounds, Mol16 and Mol42, exhibit small $\Phi_n$ for acetonitrile and have structures that are characteristic for molecular rotors. The emission quantum yield of Mol16 increases from about 0.002 to 0.015 when the media viscosity increases from about <1 cP to about 1,000 cP (see FIG. 7A), but $\Phi_{fl}$ does not exhibit any dependence on solvent polarity (see FIG. 7B). Conversely, $\Phi_{fl}$ of Mol42 does not manifest viscosity dependence (see FIG. 7C). The decrease in media polarity, however, causes about an order of magnitude increase in $\Phi_{fl}$ for Mol42 (see FIG. 7D).

For Mol16, most likely the rotation around the bond connecting the indole ring with the fluorophenyl affects the emission quantum yield. The indole moiety appears to be the principal fluorophore of Mol16. In similarity with Thioflavin T, restricting the torsional motion involving bond between the electron-donating indole and the electron-accepting flurophenyl should cause an orders-of-magnitude increase in $\Phi_{fl}$, which is consistent with our observations.

For Mol42, on the other hand, the findings suggest that the molecular motions, such as the torsional modes involving single bonds between conjugated moieties, do not detectably affect the kinetics of non-radiative deactivation of the photoexcited Mol42. The $\Phi_{fl}$ dependence on media polarity suggests that states with a strong charge-transfer character are involved in the non-radiative deactivation of the excited state of Mol42. An increase in solvent polarity stabilizes such polar sates lowering their energies bringing them close to the ground state, thus improving the efficiency of inter-system crossing. Hydrogen bonding between the carbonyl oxygen of the pyridone and the nitrogen of the amide attached to it, provide a structural motif that may make the photophysics of this fluorophore sensitive to the media polarity. Therefore, Mol16 and Mol42 provide an optical means for testing orthogonal properties of the protein binding cavity.

The fluorescence properties of topperforming molecules in the presence of C3d were also evaluated. Often, when small molecule fluorophores bind to their targets, fluorescence may be quenched, an undesirable property for potential diagnostic molecules. In the presence of increasing concentrations of C3d, no significant quenching was observed for any of the tested molecules. Remarkably, Mol4 underwent drastic fluorescence enhancement in the presence of C3d, with up to 5-fold higher fluorescence at subsaturating concentrations of C3d (FIG. 14).

Iterative molecule improvement. Based on the results of the initial virtual screen, and the identification of C3d-binding compounds via microscale thermophoresis, improvements in C3d binding affinity were sought. Using the ten top molecules additional molecules with structural similarity were identified. Furthermore, due to issues with poor molecule solubility, an additional filter for predicted log P values (log P<3) were incorporated, to eliminate very hydrophobic molecules. Finally, the newly identified set of molecules was docked to 40 distinct C3d conformations. Molecules with highest affinities to single C3d conformations and highest mean binding affinities (to all C3d conformations) were selected. All molecules that were predicted to bind as well or better to C3d as compared to our hits from the first round of screening and binding were kept. From this screen, a molecule with 15-fold improved affinity ($K_D$=1.7 µM) compared to the top molecule from the initial screen was identified (see FIG. 8).

Figure 10:
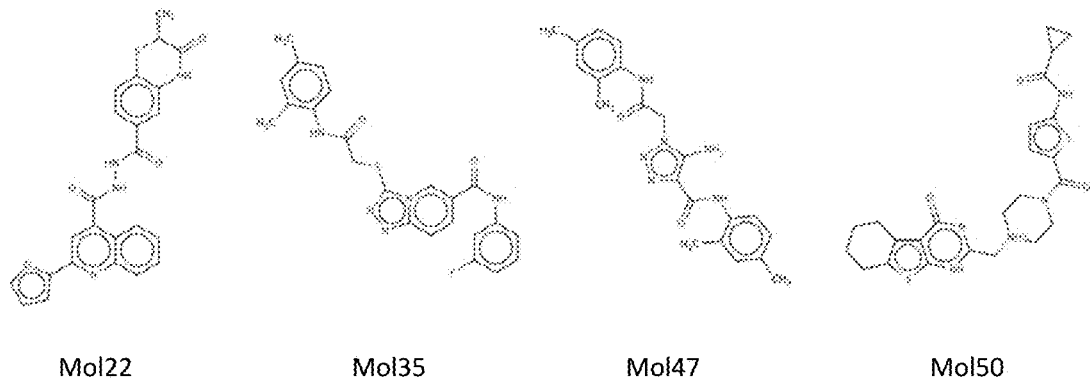
FIG. 10 presents the structures of four C3d-binding compounds.

Identifying Lead Compounds by Virtual and In Vitro Screening: Virtual screening of complement C3d, using crystallographic structures of free C3d (PDB code 1C3D) and the C3d-CR2 complex (PDB code 3OED) was used to guide the search for binding molecules. Virtual screening was performed in stages. First, molecules with chemical and geometric similarity to regions of CR2 were identified through pharmacophore screening, using Phase (Schrodinger, LLC). Pharmacophore hits were docked to C3d using AutoDock Vina, and docked poses were ranked according to predicted binding energies. Molecular dynamics simulations were performed with NAMD, to explore the dynamics of C3d-CR2 interactions, and to account for receptor flexibility during docking. 50 molecules were selected for experimental testing. Four lead compounds were identified that have in vitro direct/competitive C3d-binding properties (see FIG. 10).

Figure 11:
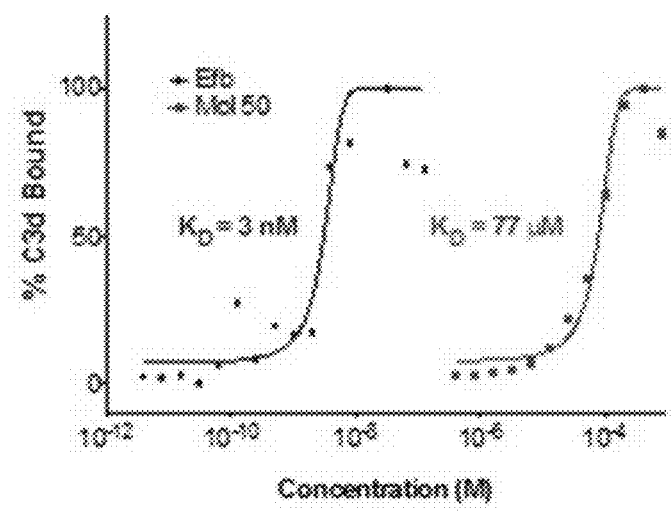
FIG. 11 presents microscale thermophoresis data, showing direct binding of Mol 50 (red) to C3d. Efb was used as a positive control (blue).

Microscale Thermophoresis: Direct binding of a small number of selected molecules was tested using microscale thermophoresis. One of the four molecules described here (Mol 50) bound to C3d with $K_D$=77 µM. We used Efb, a protein secreted from Staphylococcus aureus that binds to C3d, as a positive control for binding ($K_D$=3 nM) (see FIG. 11).

Competitive binding ELISA: 50 molecules selected from virtual screening were tested for competitive binding against C3d and its interactions with endogenous protein CR2 and bacterial protein Ecb (homolog to Efb) from *Staphylococcus aureus*. ELISA plates were coated with CR2 or Ecb for 1 hour at 37° C. Plates were washed and blocked, then incubated with serial dilutions of C3d, with and without test molecules. Plates were incubated with a mouse monoclonal antibody against C3d, followed by a horseradish peroxidase-labeled anti-mouse IgG antibody. The amount of labeled antibody (and in turn, C3d) bound was detected via reaction with a substrate solution, followed by spectrophotometric measurement. Mol 22 and 35 inhibit both C3d-CR2 and C3d-Ecb interactions, while Mol 47 only inhibits the C3d-Ecb interaction (see FIG. 12).

Fluorescence measurements. In order to use the described molecules as biomarkers, they must be detectable by an imaging modality. Since many small chemical compounds contain aromatic rings, they often exhibit intrinsic fluorescent properties. Molecules were tested for fluorescent properties, by obtaining excitation and emission spectra. Two of compounds tested, exhibited fluorescent properties (see FIG. 13).

Figure 15J:
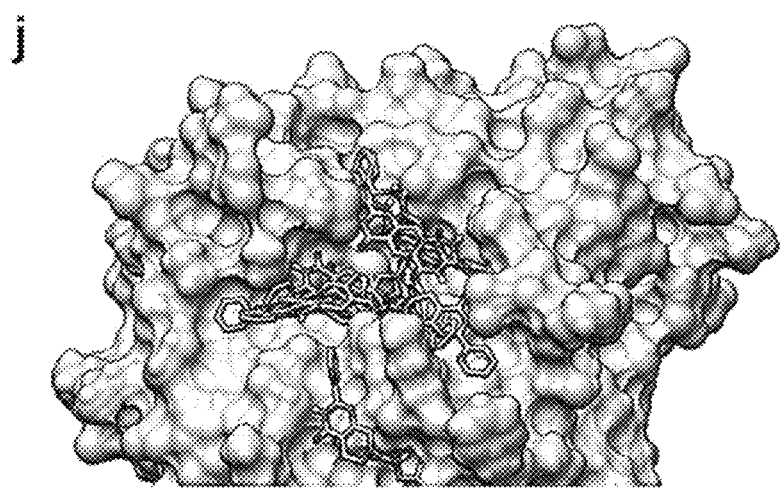
Figure 17:
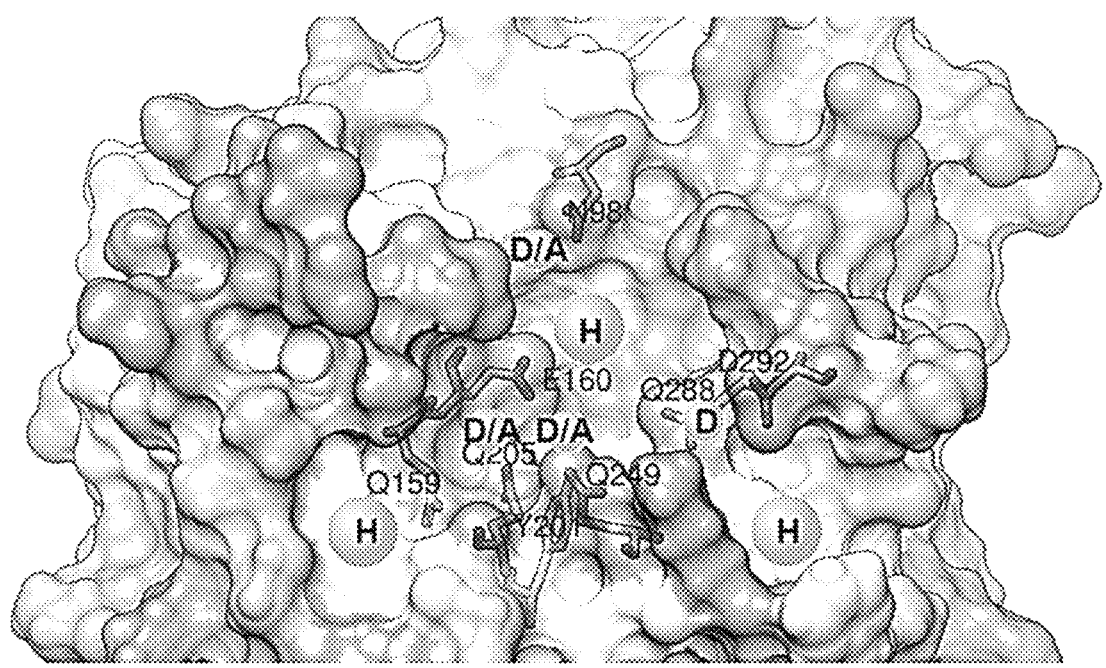
FIG. 17 shows potential pharmacophore based on docked C3d-binding molecule poses. C3d is shown as a molecular surface, colored by hydrophobicity, with gray (polar) and white (hydrophobic). Residues involved in hydrogen bonds with more than 5 ligands are shown as sticks and labeled. The seven yellow circles represent potential pharmacophore features based on how we observed docked ligands to interact with C3d. (H=hydrophobic/aromatic, D/A=hydrogen bond donor or acceptor, D=hydrogen bond donor).

Through examination of the docked binding poses of the 10 C3d-binding molecules, it is evident that, in general, all molecules bind in and around the deep cavity in the C3d surface (FIG. 15). There is great diversity in binding modes (even among different poses of a single molecule), but most molecules occupy the center of the cavity and stretch either through the "channels" that run southwest or southeast from the central cavity, or upward along the wall into sectors 2 and 3 (northwest from the central cavity). These molecules share conserved hydrogen bonding interactions, mediated by several key C3d residues surrounding the central cavity (FIG. 16). Interestingly, although experiments were performed to identify molecules that interacted with C3d in a similar manner to CR2, most molecules bound deep within the C3d cavity. Thus, efforts should focus on the cavity and channels of C3d, at least for potential diagnostic molecules, where binding (and not inhibition) is sufficient. On the basis of the structures of C3d binding molecules and analysis of molecule docking, one can redesign pharmacophore models for further structure-based optimization. FIG. 17 shows the surface of C3d with seven mock pharmacophore features, representing important hydrophobic contacts and hydrogen bonding interactions conserved largely among C3d-binding molecules. In conjunction, more precise determination of molecule binding mode, via extensive molecular dynamics simulations, NMR, or optimally crystallographic structures of C3d-ligand complexes, will facilitate further structure-based optimization. This information can be used to improve molecule binding to C3d.

A number of embodiments have been described herein. Nevertheless, it will be understood that various modifications may be made without departing from the spirit and scope of this disclosure. Accordingly, other embodiments are within the scope of the following claims.

What is claimed is:

1. A pharmaceutical composition comprising a pharmaceutically acceptable excipient and/or diluent and a C3d-binding compound capable of complexing with complement component 3d (C3d) with a $K_d$ less than 100 μM, wherein the C3d-binding compound is selected from:

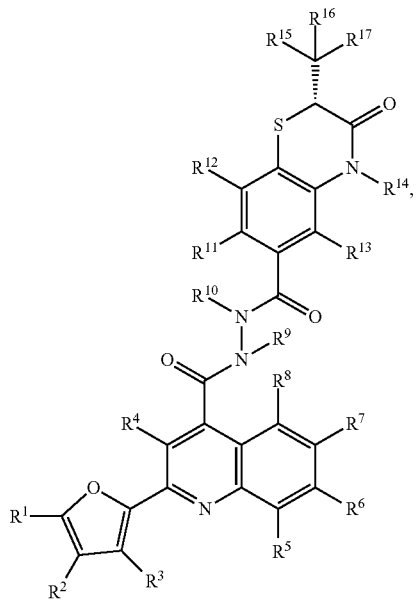

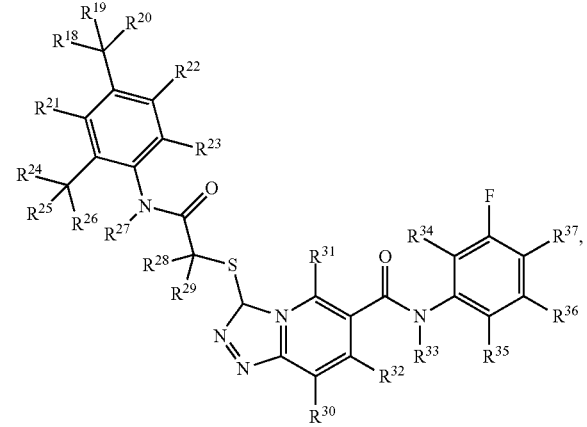

-continued

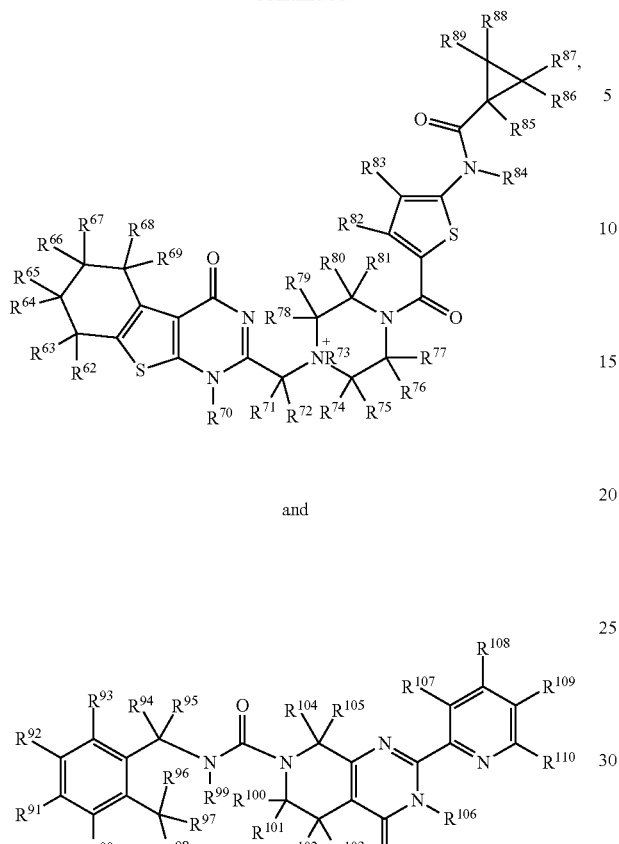

and wherein, $R^1$-$R^{110}$ is independently selected from H, D, optionally substituted ($C_1$-$C_6$)alkyl, optionally substituted hetero-($C_1$-$C_6$)alkyl, optionally substituted ($C_1$-$C_6$) alkenyl, optionally substituted hetero-($C_1$-$C_6$)alkenyl, optionally substituted ($C_1$-$C_6$)alkynyl, optionally substituted hetero-($C_1$-$C_6$)alkynyl, optionally substituted ($C_1$-$C_6$)cycloalkyl, optionally substituted ($C_1$-$C_6$)cycloalkenyl, optionally substituted aryl, optionally substituted heterocycle, hydroxyl, halo, imine, amine, amide, nitro, nitroso, nitrile, isocyanate, alkoxide, ester, carbonyl, carboxyl, thiol, SH, $SR^1$, thionyl, sulfonyl, $SiR^1_3$, $PR^1_3$, and heterocycle.

2. The pharmaceutical composition of claim 1, wherein the compound is capable of complexing with C3d with a $K_d$ less than 2 μM.

3. The pharmaceutical composition of claim 1, wherein at least one of the 3 to 7 ring structures of the compound is heteroaromatic.

4. The pharmaceutical composition of claim 1, wherein the compound has at least four nitrogen atoms.

5. The pharmaceutical composition of claim 1, wherein the compound has at least 2 amide bonds.

6. The pharmaceutical composition of claim 1, wherein the compound has florescence properties.

7. The pharmaceutical composition of claim 1, wherein the compound has a structure selected from:

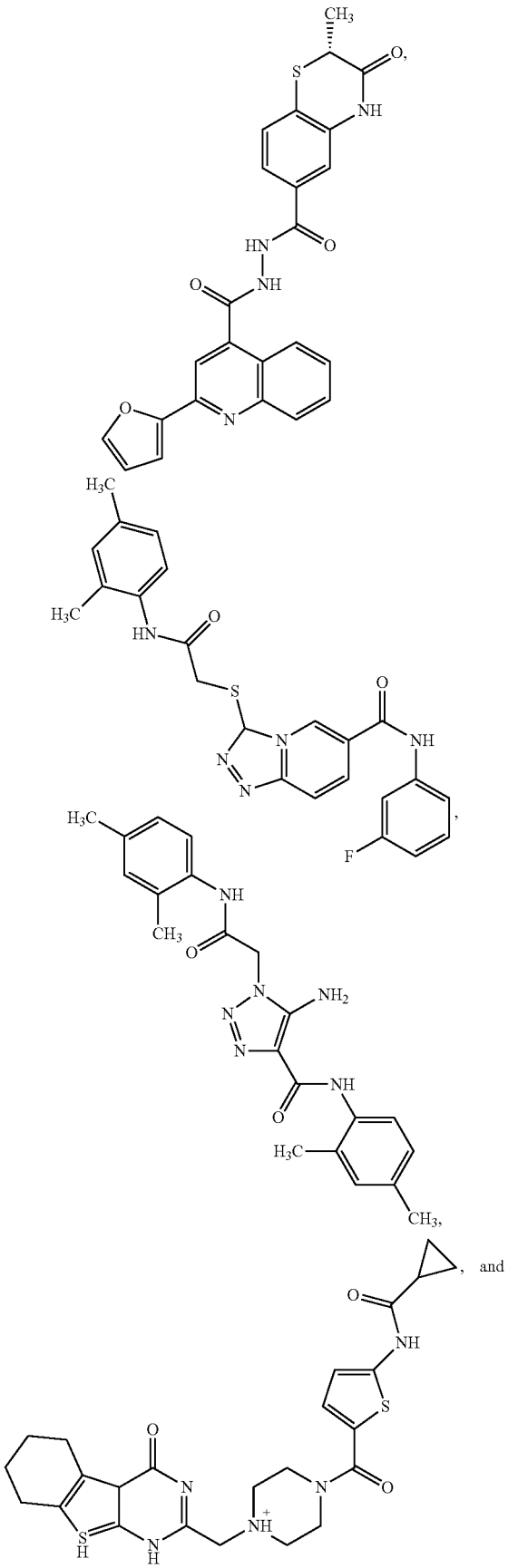

-continued

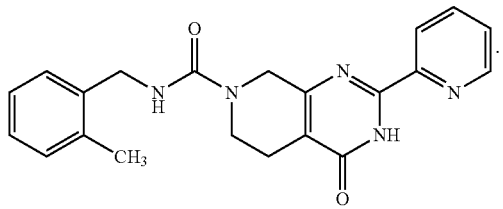

8. The pharmaceutical composition of claim 7, wherein the derivative has substantially the same structure but 1 to 4 of the functional groups has been modified or changed, wherein the derivative is further characterized by increased binding affinity for C3d and/or improved fluorescence properties.

9. The pharmaceutical composition of claim 8, wherein the improved fluorescent properties is exhibiting low quantum yield in its free (unbound) state, and undergoing a significant increase in quantum yield upon binding to C3d.

10. The pharmaceutical composition of claim 1, wherein the composition is used to locate sites of complement activation, quantify the degree of complement activation, and to target therapeutic molecules to sites of complement-mediated inflammation.

11. A method of treating a complement-mediated disease or disorder in a subject, or the amelioration of the pathophysiology of diseases or disorders caused by the overactivity of the complement system in subject, comprising administering the pharmaceutical composition of claim 1, wherein the complement-mediated disease or disorder is selected from age-related macular degeneration, systemic lupus, rheumatoid arthritis, glomerulonephritis, psoriasis, asthma, Alzheimer's disease, Huntington's disease, Parkinson's disease, age-related macular degeneration, membranoproliferative glomerulonephritis Type 2, atypical hemolytic uremic syndrome, hereditary angioedema, accelerated atherosclerosis, and paroxysmal nocturnal hemoglobinuria.

12. The method of claim 11, wherein the complement-mediated disease or disorder is age-related macular degeneration and wherein the compound further allows for localization of C3d in a subject's eye(s) by fluorescence.

13. The method of claim 12, where the pharmaceutical composition is formulated for intravitreal injection, sub-tenon injection, or topical administration.

14. A method of diagnosing or detecting a complement mediated disease or disorder, comprising administering a pharmaceutical composition of claim 1 and measuring the binding of the C3d-binding compound to C3d by detecting fluorescence wherein a localized increase in fluorescence in indicative of the complement mediated disease or disorder.

15. A C3d-binding compound selected from:

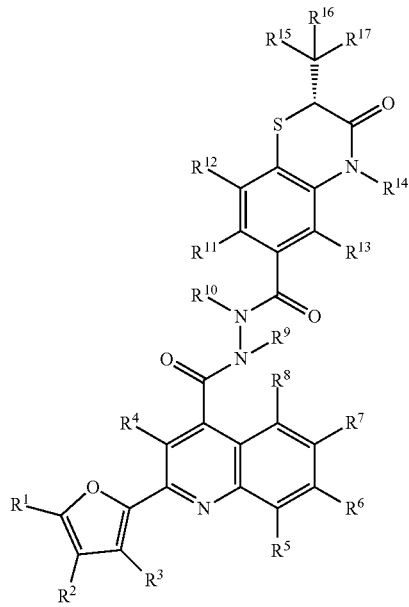

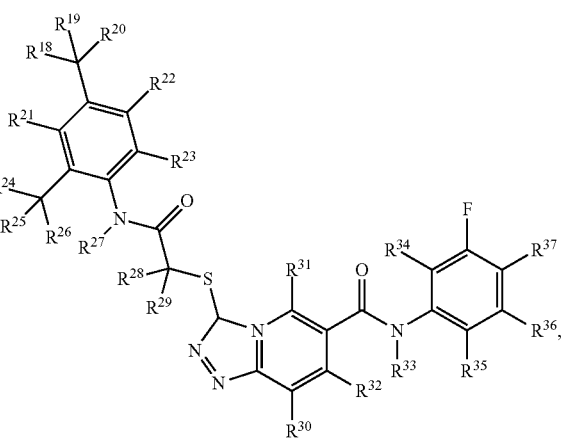

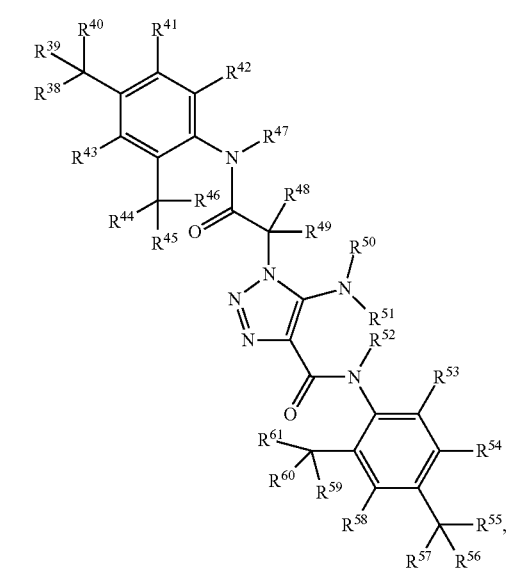

-continued

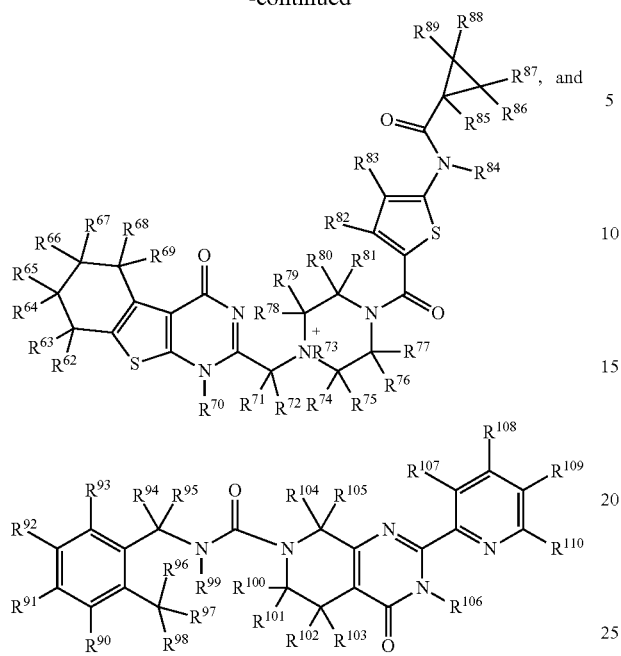

wherein,

R¹-R¹¹⁰ is independently selected from H, D, optionally substituted $(C_1-C_6)$alkyl, optionally substituted hetero-$(C_1-C_6)$alkyl, optionally substituted $(C_1-C_6)$alkenyl, optionally substituted hetero-$(C_1-C_6)$alkenyl, optionally substituted $(C_1-C_6)$alkynyl, optionally substituted hetero-$(C_1-C_6)$alkynyl, optionally substituted $(C_1-C_6)$cycloalkyl, optionally substituted $(C_1-C_6)$cycloalkenyl, optionally substituted aryl, optionally substituted heterocycle, hydroxyl, halo, imine, amine, amide, nitro, nitroso, nitrile, isocyanate, alkoxide, ester, carbonyl, carboxyl, thiol, SH, SR¹, thionyl, sulfonyl, SiR¹₃, PR¹₃, and heterocycle.

16. The Cd3-binding compound of claim 15, wherein the compound is selected form the group consisting of:

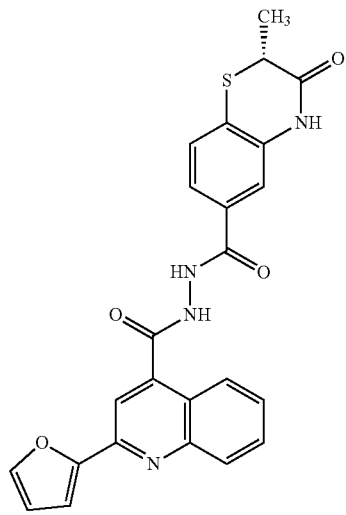

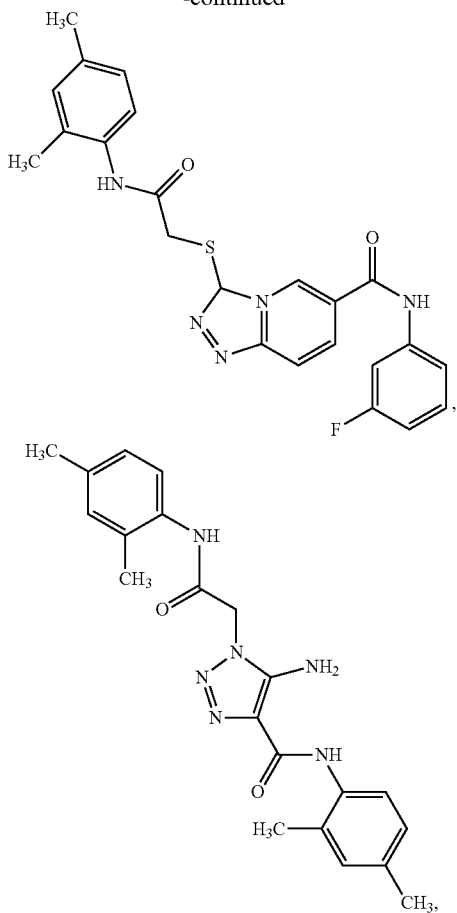

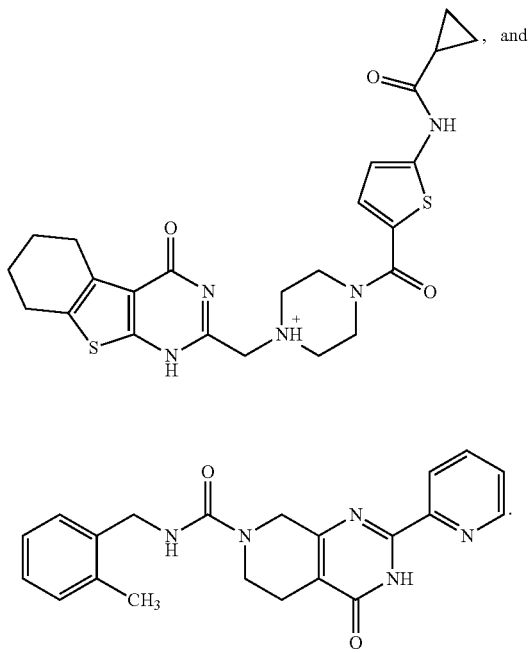

* * * * *